United States Patent
Weiner et al.

(10) Patent No.: US 10,273,472 B2
(45) Date of Patent: Apr. 30, 2019

(54) METHODS OF UTILIZING RECOMBINATION FOR THE IDENTIFICATION OF BINDING MOIETIES

(71) Applicant: AxioMx, Inc., Branford, CT (US)

(72) Inventors: Michael Weiner, Branford, CT (US); Margaret Kiss, Westbrook, CT (US)

(73) Assignee: AxioMx, Inc., Branford, CT (US)

( * ) Notice: Subject to any disclaimer, the term of this patent is extended or adjusted under 35 U.S.C. 154(b) by 163 days.

(21) Appl. No.: 15/039,682

(22) PCT Filed: Dec. 4, 2014

(86) PCT No.: PCT/US2014/068595
§ 371 (c)(1),
(2) Date: May 26, 2016

(87) PCT Pub. No.: WO2015/085079
PCT Pub. Date: Jun. 11, 2015

(65) Prior Publication Data
US 2017/0029811 A1  Feb. 2, 2017

Related U.S. Application Data

(60) Provisional application No. 61/911,744, filed on Dec. 4, 2013.

(51) Int. Cl.
*C40B 30/04* (2006.01)
*C12N 15/10* (2006.01)
*C07K 16/00* (2006.01)

(52) U.S. Cl.
CPC .......... *C12N 15/1037* (2013.01); *C07K 16/00* (2013.01); *C07K 2317/622* (2013.01); *C40B 30/04* (2013.01)

(58) Field of Classification Search
None
See application file for complete search history.

(56) References Cited

U.S. PATENT DOCUMENTS

| 2003/0148264 A1 | 8/2003 | Held et al. |
| 2007/0128165 A1 | 6/2007 | Graham et al. |
| 2011/0243979 A1 | 10/2011 | Glenn et al. |
| 2012/0015382 A1 | 1/2012 | Weitz et al. |
| 2013/0017210 A1 | 1/2013 | Peabody et al. |

FOREIGN PATENT DOCUMENTS

WO  WO-02/00729 A2  1/2002

OTHER PUBLICATIONS

International Search Report and Written Opinion for International Patent Application No. PCT/US14/68595, dated Jun. 10, 2015 (30 pages).
International Preliminary Report on Patentability for International Patent Application No. PCT/US14/68595, dated Jun. 7, 2016 (18 pages).

(Continued)

*Primary Examiner* — Christian C Boesen
(74) *Attorney, Agent, or Firm* — Clark & Elbing LLP

(57) ABSTRACT

The identification of binding moieties capable of selectively interacting with one or more target antigens is of scientific, medical, and commercial value. Disclosed herein are methods and compositions for the identification, labeling, and/or retrieval of cognate binding moieties.

17 Claims, 11 Drawing Sheets
Specification includes a Sequence Listing.

(56) References Cited

OTHER PUBLICATIONS

Benhar et al., "Highly efficient selection of phage antibodies mediated by display of antigen as Lpp-OmpA' fusions on live bacteria," J Mol Biol. 301(4):893-904 (2000).
Gebauer et al., "Engineered protein scaffolds as next-generation antibody therapeutics," Curr Opin Chem Biol. 13(3):245-55 (2009).
Loew et al., "Improved Tet-responsive promoter with minimized background expression," BMB Biotechnol. 10:81 (2010) (13 pages).
Azzazy et al., "Phage display technology: clinical applications and recent innovations," Clin Biochem. 35(6):425-45 (2002).
Bazan et al., "Phage display—a powerful technique for immunotherapy: 1. Introduction and potential of therapeutic applications," Hum Vaccin Immunother. 8(12):1817-28 (2012).
Bieniasz, "Late budding domains and host proteins in enveloped virus release," Virology. 344(1):55-63 (2006).
Extended European Search Report for European Application No. 14867475.7, dated May 9, 2017 (7 pages).
Huang et al., "Generating recombinant antibodies to membrane proteins through phage display," Antibodies. 5(2):11 (2016) (17 pages).

Fig. 4

Use of amino acid wobble position
for encoding and retrieving CDRs $P_{Forward(GAC)} \rightarrow$ SEQ ID NO 7  CGCATGCAGTGCAGCTGGGACAC                                                        framework$_{n+1}$
SEQ ID NO 8  GCGTACGTCACGTCGACCCTGTGCACGTCACCTGAATGTA ··· / CDR$_n$ / ··· AAATGTCACGTACGGCGTCACGTCA
             framework$_n$                                        SEQ ID NO 9  GTGCATGCCGCAGTGCAGT
                                                                              $\leftarrow P_{Reverse(GCG)}$ DNA sequence of first 18 bases gives CDR ID
Gray = wobble base

Fig. 8 attR x 2 (5' to 3' frames 2 and 3)

SEQUENCE LISTING

```
<160> NUMBER OF SEQ ID NOS: 31

<210> SEQ ID NO 1
<211> LENGTH: 32
<212> TYPE: DNA
<213> ORGANISM: Artificial Sequence
<220> FEATURE:
<223> OTHER INFORMATION: Synthetic Construct

<400> SEQUENCE: 1
ctaccagtat caatggtaac accagcacga gg                                    32

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct

<400> SEQUENCE: 2
ctcccagtat caatggtaac accagcacga gg                                    32

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
ctccccgtat caatggtaac accagcacga gg                                    32

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
cttcctgttt ctatggttac tcctgctcgt gg                                    32

<210> SEQ ID NO 5
<211> LENGTH: 32
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
```

```
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 5
ctnccngtnt cnatggtnac nccngcncgn gg                                32

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Leu Pro Val Ser Met Val Thr Pro Ala Arg Gly
1               5                   10

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
cgcatgcagt gcagctggga cac                                         23

<210> SEQ ID NO 8
<211> LENGTH: 65
<212> TYPE: DNA
<213> ORGANISM: Artificial Sequence
<220> FEATURE:
<223> OTHER INFORMATION: Synthetic Construct

<400> SEQUENCE: 8
gcgtacgtca cgtcgaccct gtgcacgtca cctgaatgta aaatgtcacg tacggcgtca  60
cgtca                                                             65

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
gtgcatgccg cagtgcagt                                              19

<210> SEQ ID NO 10
<211> LENGTH: 46
<212> TYPE: DNA
<213> ORGANISM: Artificial Sequence
<220> FEATURE:
<223> OTHER INFORMATION: Synthetic Construct

<400> SEQUENCE: 10
```
cgcgtctcat agctcgattc aagctgctga gctttgcaaa cctgtc            46

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
cgtcgactgg ctctcgcgcg cagagagaca taagttcgat                   40

<210> SEQ ID NO 12
<211> LENGTH: 40
<212> TYPE: DNA
<213> ORGANISM: Artificial Sequence
<220> FEATURE:
<223> OTHER INFORMATION: Synthetic Construct

<400> SEQUENCE: 12
cgatgcccga tgtttaaggc agagaccgcg tctcatagct                   40

<210> SEQ ID NO 13
<211> LENGTH: 45
<212> TYPE: DNA
<213> ORGANISM: Artificial Sequence
<220> FEATURE:
<223> OTHER INFORMATION: Synthetic Construct

<400> SEQUENCE: 13
cgattcaagc tgctgagctt tgcaaacctg tcacgtgcac gtcga             45

<210> SEQ ID NO 14
<211> LENGTH: 53
<212> TYPE: DNA
<213> ORGANISM: Artificial Sequence
<220> FEATURE:
<223> OTHER INFORMATION: Synthetic Construct

<400> SEQUENCE: 14
ctggctctcg cgcgcagaga gacataagtt cgatcgatgc cgatgtttaa agg    53

<210> SEQ ID NO 15
<211> LENGTH: 47
<212> TYPE: DNA
<213> ORGANISM: Artificial Sequence
<220> FEATURE:
<223> OTHER INFORMATION: Synthetic Construct

<400> SEQUENCE: 15
cgcgtctcat agctcgattc aagctgctga gctttgcaaa cctgtca           47

<210> SEQ ID NO 16
<211> LENGTH: 37
<212> TYPE: DNA
<213> ORGANISM: Artificial Sequence
<220> FEATURE:
<223> OTHER INFORMATION: Synthetic Construct

<400> SEQUENCE: 16
cgtgcacgtc gactggctct cgcgcgcaga gagacat                      37

<210> SEQ ID NO 17
<211> LENGTH: 35
<212> TYPE: DNA

<213> ORGANISM: Artificial Sequence
<220> FEATURE:
<223> OTHER INFORMATION: Synthetic Construct

<400> SEQUENCE: 17
aagttcgatc gatgcccgat gtttaaggca gagac        35

<210> SEQ ID NO 18
<211> LENGTH: 51
<212> TYPE: DNA
<213> ORGANISM: Artificial Sequence
<220> FEATURE:
<223> OTHER INFORMATION: Synthetic Construct

<400> SEQUENCE: 18
cgcgtctcat agctcgattc aagctgctga gctttgcaaa cctgtcacac g        51

<210> SEQ ID NO 19
<211> LENGTH: 45
<212> TYPE: DNA
<213> ORGANISM: Artificial Sequence
<220> FEATURE:
<223> OTHER INFORMATION: Synthetic Construct

<400> SEQUENCE: 19
tcgactggct ctcgcgcgca gagagacata agttcgatcg atgcc        45

<210> SEQ ID NO 20
<211> LENGTH: 13
<212> TYPE: PRT
<213> ORGANISM: Artificial Sequence
<220> FEATURE:
<223> OTHER INFORMATION: Synthetic Construct

<400> SEQUENCE: 20

Pro Thr Gly Val Thr Phe Glu Phe Ser Ser Trp Gly Gly
1               5                   10

<210> SEQ ID NO 21
<211> LENGTH: 89
<212> TYPE: DNA
<213> ORGANISM: Artificial Sequence
<220> FEATURE:
<223> OTHER INFORMATION: Synthetic Construct

<400> SEQUENCE: 21
tcatcggtcg tataatttgt ggaaggagga ggccaccatg ccccaactgg ggtaaccttt        60
gagttctcta gttgggggga taataataa        89

<210> SEQ ID NO 22
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (43)..(43)
<223> OTHER INFORMATION: v is c or t

<400> SEQUENCE: 22
ggtgccaggg cgtgcccttg ggctccccgg gcgcgtactg aavtatacaa a        51

<210> SEQ ID NO 23
<211> LENGTH: 17
<212> TYPE: PRT

<213> ORGANISM: Artificial Sequence
<220> FEATURE:
<223> OTHER INFORMATION: Synthetic Construct

<400> SEQUENCE: 23

Val Pro Gly Arg Ala Leu Gly Leu Pro Gly Arg Val Thr Asn Tyr Thr
1               5                   10                  15
Lys

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Pro Thr Gly Val Thr Phe Gly Leu Pro Gly Arg Val Thr Asn Tyr Thr
1               5                   10                  15
Lys

<210> SEQ ID NO 25
<211> LENGTH: 93
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (84)..(84)
<223> OTHER INFORMATION: v is c or t

<400> SEQUENCE: 25
tcatcggtcg tataatttgt ggaaggagga ggccaccatg ccccaactgg ggtaaccttt      60
gggctccccg ggcgcgtact gaavtataca aaa                                  93

<210> SEQ ID NO 26
<211> LENGTH: 39
<212> TYPE: DNA
<213> ORGANISM: Artificial Sequence
<220> FEATURE:
<223> OTHER INFORMATION: Synthetic Construct

<400> SEQUENCE: 26
ccccaactgg ggtaaccttt gggctccccg ggcgcgtac                             39

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Pro Asn Trp Gly Asn Leu Trp Ala Pro Arg Ala Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

```
Pro Thr Gly Val Thr Phe Gly Leu Pro Gly Arg Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Construct

<400> SEQUENCE: 29

Val Arg Ala Arg Gly Ala Gln Arg Leu Pro Gln Leu Gly
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Tyr Ala Pro Gly Glu Pro Lys Gly Tyr Pro Ser Trp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Thr Arg Pro Gly Ser Pro Lys Val Thr Pro Val Gly
1               5                   10
```

METHODS OF UTILIZING RECOMBINATION FOR THE IDENTIFICATION OF BINDING MOIETIES

BACKGROUND OF THE INVENTION

Various methods have been utilized for the identification of binding moieties capable of binding particular antigens. Prior art methods have utilized techniques including phage display, ribosome display, Phage Emulsion, Secretion, and Capture (ESCape), and rational design to identify binding moieties capable of binding particular antigens. One challenge of identifying binding moieties is that it may be difficult to identify multiple binding moieties of multiple antigens in a single reaction. There thus exists a need for methods capable of identifying multiple binding moieties of multiple antigens in a single reaction.

SUMMARY OF THE INVENTION

The present invention provides methods and compositions for the identification of one or more cognate binding moieties of one or more antigens. The invention further features methods and compositions for wobble base barcoding of nucleic acids. In addition, the invention features methods for generating libraries of nucleic acid variants encoding, e.g., a plurality of antibodies and/or fragments thereof and for increasing transformation efficiency and recombination rate in, for example, bacterial cells.

A first aspect of the present invention is a method of identifying a cognate binding moiety of one or more antigens including a first step of providing (1) a population of cells, each of the cells including (i) a cell surface antigen and (ii) a nucleic acid including a first recombination motif, and (2) a plurality of attachment-defective virions, each of the virions including (i) one of a plurality of transgenic viral surface binding moieties and (ii) a nucleic acid including a second recombination motif capable of integrating with the first motif. This aspect further includes a second step of contacting the population of cells with the virions, such that, if one or more of the virions include a cognate binding moiety of one or more of the cell surface antigens, binding of the cell surface antigen and the cognate binding moiety results in selective infection by the bound virion of the cell including the cell surface antigen of the cognate binding moiety. A third step includes incubating the population of cells under conditions sufficient to allow recombination between the first and second recombination motifs in infected cells, thereby generating a recombinant product. A fourth step includes identifying a cognate binding moiety of one or more of the antigens by identifying the nucleic acid sequence of the recombinant product or an identifying fragment thereof, in a cell, and identifying from the nucleic acid sequence an antigen and a cognate binding moiety.

In particular embodiments, the cell includes a recombination enzyme. In certain embodiments, the nucleic acid included by one or more of the virions encodes a recombination enzyme and the incubation is sufficient to allow expression of the encoded recombination enzyme. In either of these embodiments, the recombination enzyme may be an integrase. In any of the above embodiments, one or more of the recombination motifs may be a site-specific recombination motif.

In particular embodiments, each of the cells includes one of a plurality of distinct cell surface antigens. In certain embodiments, one or more of the cell surface antigens is transgenic.

A second aspect of the present invention is a method of identifying a cognate binding moiety of each of a plurality of antigens, including a first step of providing (1) a population of cells, each of the cells including (i) one of a plurality of transgenic cell surface antigens, (ii) a nucleic acid including a first marker gene fragment adjacent to a first site-specific recombination motif, and (iii) a recombination enzyme, and (2) a plurality of attachment-defective virions, each of the virions including (i) one of a plurality of transgenic viral surface binding moieties and (ii) a nucleic acid including a second marker gene fragment adjacent to a second site-specific recombination motif capable of integrating with the first motif, such that the first marker gene fragment and the second marker gene fragment are positioned such that site-specific recombination between the first and second motif will result in a functional marker gene. This aspect further includes a second step of contacting the population of cells with the virions, such that, if one or more of the virions include a cognate binding moiety of one or more of the cell surface antigens, binding of the cell surface antigen and the cognate binding moiety results in selective infection by the bound virion of the cell including the cell surface antigen of the cognate binding moiety. A third step includes incubating the population of cells under conditions sufficient to allow site-specific recombination between the first and second site-specific recombination motifs in infected cells, thereby generating a recombinant product capable of expressing a functional marker protein. A fourth step includes incubating the population of cells in a manner sufficient to allow detection of cells having a phenotype resulting from expression of the functional marker protein. A fifth step includes isolating one or more cells having the detectable phenotype. A sixth step includes identifying a cognate binding moiety of one or more of the antigens by identifying the nucleic acid sequence of the recombinant product or an identifying fragment thereof, in one or more of the isolated cells, and identifying from the nucleic acid sequence an antigen and a cognate binding moiety.

In some embodiments, one or more of the first marker gene fragments or one or more of the second marker gene fragments include a functional marker gene promoter and one or more of the first marker gene fragments or one or more of the second marker gene fragments include a coding segment of the same functional marker gene. In particular embodiments, one of the first marker gene fragment or the second marker gene fragment includes a promoter gene fragment and the other includes a coding gene fragment. In certain embodiments, one of the first marker gene fragment or the second marker gene fragment includes a promoter gene fragment and a 5' coding gene fragment and the other includes a 3' coding gene fragment. In some embodiments, the first marker gene fragments and second marker gene fragments can each encode subunits of a multimeric protein, which can form a complex that, for example, results in activation or inhibition of a cellular function, e.g., a function that results in a detectable phenotype or identifiable phenotype such as described herein. In alternate embodiments, the first marker gene fragments and second marker gene fragments can include segments of an aptamer, RNAi molecule (e.g., an siRNA), or CRISPR molecule, e.g., such that recombination between a first marker gene fragment and a second marker gene fragment results in the production of the aptamer, RNAi molecule (e.g., an siRNA), or CRISPR molecule. In further embodiments, the first marker gene fragments and second marker gene fragments can encode fragments of a protein capable of producing an identifiable activity and/or phenotype. In particular embodiments, the first marker gene fragment encodes an activation domain and the second marker gene fragment encodes a DNA binding domain, such that the resultant protein products can cooperate to induce transcription of a gene within the cell (e.g., a gene activating a detectable phenotype or identifiable phenotype such as described herein).

In any of the above embodiments of this aspect, the marker gene may be an antibiotic resistance gene. In particular embodiments, the antibiotic resistance gene is an ampicillin resistance gene. In some embodiments, the marker gene encodes a fluorescent protein.

In certain embodiments, the polynucleotide sequence of one or more of the transgenic cell surface antigens is adjacent to a first marker gene fragment. In particular embodiments, the polynucleotide sequence of one or more of the transgenic viral surface binding moieties is adjacent to a second marker gene fragment.

In some embodiments, the recombination enzyme is an integrase. In some embodiments, one or more of the transgenic cell surface antigens are included by a cell surface antigen fusion protein. In particular embodiments, one or more of the cell surface antigen fusion proteins include an *E. coli* F pilin protein or a fragment thereof capable of displaying the antigen.

In any of the above embodiments, one or more of the transgenic viral surface binding moieties may be viral surface binding moiety fusion proteins. In any of the above embodiments, the cells may be bacterial, yeast, or mammalian cells. In any of the above embodiments, the virions may be attachment-defective bacteriophage, baculovirus, or adenovirus virions. Optionally, the virion may transfer one or more genetic elements into the cell upon infection of the cell, and the genetic elements may optionally encode an F pilus polypeptide. In any of the above embodiments, the virions may be M13 phage lacking Gp3. In any of the above embodiments, the virions may be baculovirus and the cells may be mammalian cells. In any of the above embodiments, the first and second recombination motifs may be att recombination motifs.

A third aspect of the present invention is a method of identifying a cognate binding moiety of each of a plurality of antigens, the method including the first step of providing (1) a population of *E. coli* cells, each of the cells including (i) a cell surface antigen::F pilin protein fusion protein, (ii) a nucleic acid including a first marker gene fragment adjacent to a first att recombination motif, and (iii) a recombination enzyme, and (2) a plurality of Gp3-defective M13 phage virions, each of the virions including (i) one of a plurality of viral surface binding moiety fusion proteins and (ii) a nucleic acid including a second marker gene fragment adjacent to a second att recombination motif capable of integrating with the first att recombination motif, such that the first marker gene fragment and the second marker gene fragment are positioned such that site-specific recombination between the att recombination motifs will result in a functional marker gene. A second step of this aspect includes contacting the population of cells with the virions, such that, if one or more of the virions include a cognate binding moiety of one or more of the cell surface antigens, binding of the cell surface antigen and the cognate binding moiety results in selective infection by the bound virion of the cell including the cell surface antigen of the cognate binding moiety. A third step includes incubating the population of cells under conditions sufficient to allow site-specific recombination between the att recombination motifs in infected cells, thereby generating a recombinant product capable of expressing a functional marker protein. A fourth step includes incubating the population of cells in a manner sufficient to allow detection of cells having a phenotype resulting from expression of the functional marker protein. A fifth step includes isolating one or more cells having the detectable phenotype. A sixth step includes identifying a cognate binding moiety of one or more of the plurality of antigens by identifying the nucleic acid sequence of the recombinant product or an identifying fragment thereof, in one or more of the isolated cells, and identifying from the nucleic acid sequence an antigen and a cognate binding moiety.

In certain embodiments, one or more of the first marker gene fragments or one or more of the second marker gene fragments include a functional marker gene promoter and one or more of the first marker gene fragments or one or more of the second marker gene fragments include a coding segment of the same functional marker gene. In particular embodiments, one of the first marker gene fragment or the second marker gene fragment includes a promoter gene fragment and the other includes a coding gene fragment. In certain embodiments, one of the first marker gene fragment or the second marker gene fragment includes a promoter gene fragment and a 5' coding gene fragment and the other includes a 3' coding gene fragment. In some instances, the marker gene is an antibiotic resistance gene, such as an ampicillin resistance gene. In other instances, the marker gene encodes a fluorescent protein.

In certain embodiments, the polynucleotide sequence of one or more of the transgenic cell surface antigens is adjacent to a first marker gene fragment. In some embodiments, the polynucleotide sequence of one or more of the transgenic viral surface binding moieties is adjacent to a second marker gene fragment. In some embodiments, the recombination enzyme is an integrase.

In any of the above embodiments, the population of cells may include a plurality of transgenic cell surface antigens including 10,000 or more distinct antigens. In any of the above embodiments, the plurality of transgenic viral surface binding moieties includes 10,000 or more distinct binding moieties.

A fourth aspect of the present invention is a method of identifying a cognate binding moiety of each of a plurality of antigens, the method including a first step of transferring into each of one or more cells (1) a first vector including (i) the sequence of an antigen fusion protein including an antigen and a first marker subunit and (ii) a first recombination motif, and (2) a second vector including (i) the sequence of a binding moiety fusion protein including a binding moiety and a second marker subunit and (ii) a second recombination motif, such that interaction of the antigen and the binding moiety results in a functional complex capable of detectably marking a cell in which the interaction occurs. A second step of this aspect includes incubating the cells in a manner allowing (1) expression of the antigen fusion protein and the binding moiety fusion protein, such that a functional marker complex will form within a cell if binding occurs between the antigen and the binding moiety, thereby detectably marking the cell, and (2) expression of a recombination enzyme, the recombination enzyme facilitating recombination between the first and second recombination motifs, thereby generating a recombinant product including the sequence of the antigen fusion protein and the sequence of the binding moiety fusion protein. A third step includes isolating one or more detectably marked cells. A fourth step includes identifying a cognate binding moiety of one or more of the plurality of antigens by identifying the nucleic acid sequence of the recombinant product or an identifying fragment thereof, in one or more of the isolated cells, and identifying from the nucleic acid sequence an antigen and a cognate binding moiety.

In particular embodiments, one of the first and second marker subunits includes a DNA recognition element and the other includes a transcriptional activation element. In certain embodiments, the functional marker complex is fluorescent or enzymatically active.

A fifth aspect of the present invention is a method of identifying a cognate binding moiety of each of a plurality of antigens, the method including the first step of transferring into each of one or more cells (1) a first vector including (i) the sequence of an antigen fusion protein including an antigen and a first marker subunit and (ii) a first recombination motif, and (2) a second vector including (i) the sequence of a binding moiety fusion protein including a binding moiety and a second marker subunit and (ii) a second recombination motif, such that interaction of the antigen and the binding moiety results in a functional complex capable of detectably marking a cell in which the interaction occurs. A second step of the present aspect includes incubating the cells in a manner allowing expression of the antigen fusion protein and the binding moiety fusion protein, such that a functional marker complex will form within a cell if binding occurs between the antigen and the binding moiety, and such that formation of the functional marker complex results in expression of a recombination enzyme, the recombination enzyme facilitating site-specific recombination between the first and second recombination motifs to generate a recombinant product including the sequence of the antigen fusion protein and the sequence of the binding moiety fusion protein. A third step includes identifying a cognate binding moiety of one or more of the plurality of antigens by identifying the recombinant product nucleic acid sequence, or identifying a fragment thereof, in from the cells, and identifying its associated cognate binding moiety.

In any embodiment of the fourth or fifth aspects of the present invention, one or more of the first and second recombination motifs may be site-specific recombination motifs, such as, e.g., att recombination motifs. In any embodiment of the fourth or fifth aspects of the present invention, the cells may be bacterial, yeast, or mammalian cells. In any embodiment of the fourth or fifth aspects of the present invention, one or more of the firsts and second vectors may be plasmids.

A sixth aspect of the present invention is a method of identifying a cognate binding moiety of one or more antigens, the method including the first step of providing (1) a population of cells, each of the cells including (i) a cell surface antigen, (ii) a nucleic acid including a first recombination motif, and (iii) a conditionally expressed infection apparatus, and (2) a plurality of virions, each of the virions including (i) one of a plurality of transgenic viral surface binding moieties and (ii) a nucleic acid including a second recombination motif capable of integrating with the first motif. A second step of the present aspect includes contacting the population of cells with the virions. A third step includes incubating the cells with the virions under conditions that are not permissive for infection but are sufficient to allow binding of one or more of the cell surface antigens by one or more of the cognate binding moieties, such that one or more of the cells are bound by one or more of the virions. A fourth step includes emulsifying the bound cells, thereby encapsulating one or more of the cells in one or more emulsion droplets. A fifth step includes incubating the emulsified cells under conditions permissive to expression of the conditionally expressed infection apparatus, thereby allowing infection of one or more of the emulsified cells by one or more virions present in the same emulsion droplet. A sixth step includes incubating the cells in a manner sufficient to allow recombination between the first and second site-specific recombination motifs in infected cells, thereby generating a recombinant product. A seventh step includes identifying a cognate binding moiety of one or more of the antigens by identifying the nucleic acid sequence of the recombinant product or an identifying fragment thereof, in a cell, and identifying from the nucleic acid sequence an antigen and a cognate binding moiety.

In certain embodiments, the cell includes a recombination enzyme. In any of the above embodiments, the nucleic acid included by one or more of the virions encodes a recombination enzyme and the incubation may be sufficient to allow expression of the encoded recombination enzyme. The recombination enzyme may be an integrase. In particular embodiments, one or more of the recombination motifs is a site-specific recombination motif.

In some embodiments each of the cells includes one of a plurality of distinct cell surface antigens. In some embodiments, one or more of the cell surface antigens are transgenic.

A seventh aspect of the present invention is a method of identifying a cognate binding moiety of one or more antigens, the method including the first step of providing (1) a population of cells, each of the cells including (i) one of a plurality of cell surface antigens, (ii) a nucleic acid including a first marker gene fragment adjacent to a first site-specific recombination motif, (iii) a recombination enzyme, and (iv) a conditionally expressed infection apparatus, and (2) a plurality of virions, each of the virions including (i) one of a plurality of transgenic viral surface binding moieties and (ii) a nucleic acid including a second marker gene fragment adjacent to a second site-specific recombination motif capable of integrating with the first motif such that the first marker gene fragment and the second marker gene fragment are positioned such that site-specific recombination between the first and second motif will result in a functional marker gene. A second step of this aspect includes contacting the population of cells with the virions. A third step includes incubating the cells with the virions under conditions that are not permissive for infection but are sufficient to allow binding of one or more of the cell surface antigens by one or more of the cognate binding moieties, such that one or more of the cells are bound by one or more of the virions. A fourth step includes emulsifying the bound cells, thereby encapsulating one or more of the cells in one or more emulsion droplets. A fifth step includes incubating the emulsified cells under conditions permissive to expression of the conditionally expressed infection apparatus, thereby allowing infection of one or more of the emulsified cells by one or more virions present in the same emulsion droplet. A sixth step includes incubating the cells in a manner sufficient to allow recombination between the first and second site-specific recombination motifs in infected cells, thereby generating a recombinant product capable of expressing a functional marker protein. A seventh step includes incubating the population of cells in a manner sufficient to allow detection of cells having a phenotype resulting from expression of the functional marker protein. An eighth step includes isolating one or more cells having the detectable phenotype. A ninth step includes identifying a cognate binding moiety of one or more of the antigens by identifying the nucleic acid sequence of the recombinant product or an identifying fragment thereof, in one or more of the isolated cells, and identifying from the nucleic acid sequence an antigen and a cognate binding moiety.

In particular embodiments, one or more of the first marker gene fragments or one or more of the second marker gene fragments include a functional marker gene promoter and one or more of the first marker gene fragments or one or more of the second marker gene fragments include a coding segment of the same functional marker gene. In certain embodiments, one of the first marker gene fragment or the second marker gene fragment includes a promoter gene fragment and the other includes a coding gene fragment. In some embodiments, of the first marker gene fragment or the second marker gene fragment includes a promoter gene fragment and a 5' coding gene fragment and the other includes a 3' coding gene fragment. In any of these embodiments, the marker gene may be an antibiotic resistance gene, such as an ampicillin resistance gene. In some embodiments, the marker gene encodes a fluorescent protein.

In some embodiments, the polynucleotide sequence of one or more of the cell surface antigens is adjacent to a first marker gene fragment. In particular embodiments, the polynucleotide sequence of one or more of the transgenic viral surface binding moieties is adjacent to a second marker gene fragment. In some embodiments, one or more of the cell surface antigens are included by a cell surface antigen fusion protein.

In any embodiment of the sixth or seventh aspect of the present invention, one or more of the transgenic viral surface binding moieties may be viral surface binding moiety fusion proteins. In any embodiment of the sixth or seventh aspect of the present invention, the cells may be bacterial, yeast, or mammalian cells. In any embodiment of the sixth or seventh aspect of the present invention, the virions may be attachment-defective bacteriophage, baculovirus, or adenovirus virions. In any embodiment of the sixth or seventh aspect of the present invention, the cells may be E. coli cells, the infection apparatus may be an F pilus apparatus, and/or the virions may be M13 bacteriophage. In any embodiment of the sixth or seventh aspect of the present invention, the virions may be attachment-defective. In any embodiment of the sixth or seventh aspect of the present invention, the emulsion further includes a cleavage reagent capable of facilitating infection under permissive conditions.

Any embodiment of the sixth or seventh aspect of the present invention may further include breaking the emulsion subsequent to the infection of one or more of the emulsified cells.

In any of the above embodiments, the antigen includes one or more modified amino acids, such as one or more phosphoserines. In any of the above embodiments, the binding moiety may be an antibody or scFv. In any of the above embodiments, one or more of the viral surface binding moieties may include one or more segments derived from the sequence of an antibody expressed by a cell of an inoculated subject. In any of the above embodiments, one or more of the viral surface binding moieties may include one or more segments derived from the sequence of an antibody expressed by a naïve cell. In any of the above embodiments, one or more of the antigens may be an antigen isolated from a pathogen. In particular embodiments, one or more antigens isolated from each of a plurality of pathogens. In any of the above embodiments, the recombinant product includes one or more variable priming sequences. In particular embodiments, the recombinant product includes two variable priming sequences that flank the sequences of the antigen and the binding moiety. In any of the above embodiments, the sequencing may be deep sequencing or NextGeneration sequencing. In any of the above embodiments, a segment of one or more polynucleotides encoding an antigen or binding moiety may be distinguished from one or more substantially identical segments by substitution at one or more nucleobases, such that the substitution does not modify the polypeptide encoded by the segment (e.g., a translationally silent substitution). In particular embodiments, one or more substituted nucleobases is a nucleobase present in a codon.

The present invention further includes a virus including a nucleic acid encoding a site-specific recombination motif, such that upon infection of a cell including a nucleic acid having a complementary site-specific recombination motif, the viral nucleic acid is capable of site-specific recombination with the nucleic acid of the cell.

A ninth aspect of the present invention is a method of identifying a cognate binding moiety of one or more antigens, the method including the steps of providing (1) a population of infection-defective cells, each of the cells including (i) one of a plurality of cell surface antigens, (ii) a nucleic acid including a first marker gene fragment adjacent to a first site-specific recombination motif, (iii) a recombination enzyme, and (iv) a virus capable of transferring one or more genes encoding the infection apparatus to cells, and (2) a plurality of virions, each of the virions including (i) one of a plurality of transgenic viral surface binding moieties and (ii) a nucleic acid including a second marker gene fragment adjacent to a second site-specific recombination motif capable of integrating with the first motif such that the first marker gene fragment and the second marker gene fragment are positioned such that site-specific recombination between the first and second motif will result in a functional marker gene. A second step of this aspect includes contacting the population of cells with the virions. A third step includes incubating the cells with the virions under conditions that are not permissive to transfer of infection apparatus genes, but are sufficient to allow binding of one or more of the cell surface antigens by one or more of the cognate binding moieties, such that one or more of the cells are bound by one or more of the virions. A fourth step includes emulsifying the bound cells, thereby encapsulating one or more of the cells in one or more emulsion droplets. A fifth step includes transferring infection apparatus genes to the emulsified cells to allow recombinant expression of the infection apparatus, thereby allowing infection of one or more of the emulsified cells by one or more virions present in the same emulsion droplet. A sixth step includes incubating the cells in a manner sufficient to allow recombination between the first and second site-specific recombination motifs in infected cells, thereby generating a recombinant product capable of expressing a functional marker protein. A seventh step includes incubating the population of cells in a manner sufficient to allow detection of cells having a phenotype resulting from expression of the functional marker protein. An eighth step includes isolating one or more cells having the detectable phenotype. A ninth step includes identifying a cognate binding moiety of one or more of the antigens by identifying the nucleic acid sequence of the recombinant product or an identifying fragment thereof, in one or more of the isolated cells, and identifying from the nucleic acid sequence an antigen and a cognate binding moiety.

A ninth aspect of the present invention is a method of identifying a cognate binding moiety of one or more antigens, the method including the steps of providing (1) a population of infection apparatus-defective cells, each of the cells including (i) a cell surface antigen, (ii) a construct capable of expressing a protein required for viral infection of the cell (e.g., an F pilin protein) in the presence of an activator, and (iii) a nucleic acid including a first recombination motif, and (2) a plurality of virions, each of the virions including (i) one of a plurality of transgenic viral surface binding moieties, and (ii) a nucleic acid including a second recombination motif capable of integrating with the first motif. A second step of this aspect includes contacting the population of cells with the virions, wherein, if one or more of the virions include a cognate binding moiety of one or more of the cell surface antigens, then the cell surface antigen binds to the cognate binding moiety. A third step includes removing unbound virions. A fourth step includes introducing an activator, thereby inducing the expression of the protein required for viral infection of the cell (e.g., the F pilin protein), the expression of the protein required for viral infection of the cell (e.g., the F pilin protein) resulting in selective infection by the bound virion of the cell including the cell surface antigen of the cognate binding moiety. A fifth step includes incubating the population of cells under conditions sufficient to allow recombination between the first and second recombination motifs in infected cells, thereby generating a recombinant product. A sixth step includes identifying a cognate binding moiety of one or more of the antigens by identifying the nucleic acid sequence of the recombinant product or an identifying fragment thereof, in a cell, and identifying from the nucleic acid sequence an antigen and a cognate binding moiety. In any embodiment of the above aspect, optionally, the activator may be tetracycline and the construct capable of expressing a protein required for viral infection of the cell (e.g., F pilin protein) in the presence of an activator may include a tetracycline responsive promoter controlling a gene encoding the protein required for viral infection of the cell (e.g., F pilin protein).

In a tenth aspect, the invention features a method of identifying a cognate binding moiety of one or more antigens including a first step of providing (1) a first population of cells, each of the cells including (i) a cell surface antigen and (ii) a nucleic acid including a first recombination motif, and (2) a second population of cells, each of cells of the second population including (i) one of a plurality of surface binding moieties and (ii) a nucleic acid including a second recombination motif capable of integrating with the first motif. This aspect further includes a second step of contacting the first population of cells with the second population of cells, such that, if one or more of the cells of the second population include a cognate binding moiety of one or more of the cell surface antigens of the first population, binding of the cell surface antigen and the cognate binding moiety results in:

(1) transfer of the two nucleic acids into the same cell (e.g., transfer of the nucleic acid including the first recombination motif into the cell from the second population, or transfer of the nucleic acid including the second recombination motif into the cell from the first population), or (2) combining of the two cells (e.g., two haploid cells) to form a daughter cell (e.g., a diploid cell) containing the two nucleic acids. A third step includes incubating the population of cells under conditions sufficient to allow recombination between the first and second recombination motifs in the cell, thereby generating a recombinant product. A fourth step includes identifying a cognate binding moiety of one or more of the antigens by identifying the nucleic acid sequence of the recombinant product or an identifying fragment thereof, e.g., in a cell, and identifying from the nucleic acid sequence an antigen and a cognate binding moiety.

In some embodiments, the first population of cells includes F+ *E. coli* and the second population of cells includes F− *E. coli*. In alternate embodiments, the first population of cells includes F− *E. coli* and the second population of cells includes F+ *E. coli*.

In other embodiments, each population of cells includes haploid cells capable of mating with haploid cells from the other population of cells. In certain embodiments, the first population of cells includes yeast of mating type a and the second population of cells includes yeast of mating type alpha. In certain embodiments, the first population of cells includes yeast of mating type alpha and the second population of cells includes yeast of mating type a. In particular embodiments, a protein required for mating (e.g., a cell surface protein) is repressed in one of the yeast mating types, binding of the binding moiety on yeast of one mating type to the cell surface marker on yeast of the other mating type occurs, and mating is induced, thereby resulting in a diploid cell containing both nucleic acids, which can then recombine, e.g., thus turning on a detectable phenotype or identifiable phenotype (e.g., expression of a selectable marker).

In further embodiments, one population of cells includes sperm and one population of cells includes eggs. In additional embodiments, one population of cells includes an intracellular pathogen capable of infecting the other population of cells. In a particular embodiment, one population of cells includes dicotylendous plant cells, and the intracellular pathogen capable of infecting the dicotylendous plant cells is *Agrobacterium tumafaciens*, also referred to as *Rhizobium radiobacter*.

Further embodiments of the tenth aspect may include, for example, any of the embodiments described above for the other aspects of the invention, in which the virion is replaced by a cell of the second population.

An eleventh aspect of the present invention is a composition including a plurality of barcoded nucleic acid variants, each nucleic acid variant encoding a polypeptide and having a sequence including (i) one or more variable codons that vary between the nucleic acid variants, and (ii) a plurality of identifier codons, each identifier codon including a nucleotide at a wobble position, such that the combination of the nucleotides at the wobble positions of the identifier codons form a barcode that identifies the sequence of the nucleic acid variant, and the nucleotides at the wobble positions of the identifier codons are translationally silent.

In some embodiments of the eleventh aspect, the barcode of each distinct nucleic acid variant differs from the barcodes of the remaining nucleic acid variants by at least one nucleotide. In further embodiments, each of the barcodes includes at least 1-10 (e.g., 1-10, 1-20, 1-30, 1-40, 1-50, 1-100, or 1-500) nucleotides. In certain embodiments, at least two of the nucleotides of the barcode of each nucleic acid variant are located in consecutive codons. In alternative embodiments, at least two of the nucleotides of the barcode of each nucleic acid variant are not located in consecutive codons.

In some embodiments, the nucleotides of the barcodes of each nucleic acid variant are located within a portion of the nucleic acid variant including up to 10,000 contiguous nucleotides (e.g., up to 3, 4, 5, 6, 7, 8, 9, 10, 20, 30, 40, 50, 60 70, 80, 90, 100, 150, 200, 300, 400, 500, 600, 700, 800, 900, 1000, 2000, 3000, 4000, 5000, 6000, 7000, 8000, 9000, or 10,000 contiguous nucleotides). In particular embodiments, the nucleic acid variants each include a double stranded nucleic acid. In certain embodiments, each of the identifier codons in a particular nucleic acid variant are located on the same strand of the double-stranded nucleic acid. In alternative embodiments, at least two of the identifier codons in a particular nucleic acid variant are located on different strands of the double-stranded nucleic acid. In further embodiments, one of the identifier codons located on different strands can be identified by sequencing the opposite strand of the double-stranded nucleic acid. In specific embodiments, at least one of the identifier codons in each nucleic acid variant encodes leucine or serine. In further embodiments, each of the nucleic acid variants further includes a check-sum codon.

In some embodiments of the eleventh aspect, each of the nucleic acid variants includes at least six identifier codons. In certain embodiments, identical nucleic acid variants include identical barcodes. In alternative embodiments, identical nucleic acid variants include distinct barcodes. In other embodiments, distinct nucleic acid variants include distinct barcodes.

In some embodiments of the eleventh aspect, the barcodes of one or more of the nucleic acid variants are identified by sequencing. In further embodiments, the sequencing produces a nucleic acid sequence read including the set of nucleotides occupying the wobble positions in the nucleic acid variants. In certain embodiments, the sequencing determines a nucleic acid sequence contig including the set of nucleotides occupying the wobble positions in the nucleic acid variants.

In alternate embodiments of the eleventh aspect, the barcodes of one or more of the nucleic acid variants are identified by single nucleotide polymorphism (SNP) genotyping.

In some embodiments of the eleventh aspect, each of the nucleic acid variants includes a nucleic acid sequence encoding a complementarity determining region (CDR). In further embodiments, each of the nucleic acid variants includes nucleic acid sequences encoding two to six CDR regions. In certain embodiments, each of the nucleic acid variants includes nucleic acid sequences encoding a CDR-H1, CDR-H2, and CDR-H3. In other embodiments, each of the nucleic acid variants includes nucleic acid sequences encoding a CDR-L1, CDR-L2, and CDR-L3. In further embodiments, each of the nucleic acid variants includes nucleic acid sequences encoding a CDR-H1, CDR-H2, CDR-H3, CDR-L1, CDR-L2, and CDR-L3. In specific embodiments, each of the nucleic acid variants includes a nucleic acid sequence encoding an scFv.

In some embodiments of the eleventh aspect, the composition includes at least six nucleic acid variants. In particular embodiments, the composition includes at least 100 nucleic acid variants. In further embodiments, the composition includes at least 1000 nucleic acid variants. In other embodiments, includes between 1000-4096 nucleic acid variants. In specific embodiments, the composition includes at least 10,000 nucleic acid variants. In certain embodiments, the composition includes between 10,000-65,000 variants.

In some embodiments of the eleventh aspect, the positions of the identifier codons are invariant between the nucleic acid variants.

A twelfth aspect of the present invention is a method of generating a library of barcoded nucleic acid variants, the method including (a) providing a plurality of nucleic acid variants, in which the amino acids encoded by one or more variable codons varies between the plurality of the nucleic acid variants, and (b) changing a nucleotide at a wobble position in each of a plurality of identifier codons within the nucleic acid variants, the identifier codons being distinct from the variable codons, such that the combination of the nucleotides at the wobble positions of the identifier codons form a barcode that identifies the sequence of the nucleic acid variant, the nucleotides at the wobble positions of the identifier codons being translationally silent.

A thirteenth aspect of the present invention is a method of selecting a nucleic acid variant from a library, the method including the first step of (a) providing a library of nucleic acid variants, each nucleic acid variant encoding a polypeptide and having a sequence including (i) one or more variable codons that vary between the nucleic acid variants, and (ii) a plurality of identifier codons, each identifier codon including a nucleotide at a wobble position, the combination of the nucleotides at the wobble positions of the identifier codons forming a barcode that identifies the sequence of the nucleic acid variant, the nucleotides at the wobble positions of the identifier codons being translationally silent. A second step (b) of this aspect includes selecting a nucleic acid variant from the library. A third step of this aspect includes identifying the nucleic acid variant selected in step (b) by its barcode.

In some embodiments of the thirteenth aspect, the method further includes isolating the nucleic acid variant selected in step (b) from the library. In particular embodiments, the isolating includes amplifying the nucleic acid variant selected in step (b) from the library. In further embodiments, the amplifying includes PCR amplification using PCR primers specific to the nucleic acid variant selected in step (b). In certain embodiments, at least a portion of the PCR primers is complementary to a portion of one or more of the barcodes identifying the nucleic acid variant selected in step (b). In specific embodiments, one of the PCR primers is complementary to a barcode located on the 5' end of the nucleic acid variant selected in step (b), and another of the PCR primers is complementary to a barcode located on the 3' end of the nucleic acid variant selected in step (b).

In some embodiments of the twelfth and thirteenth aspects, the barcode of each distinct nucleic acid variant differs from the barcodes of the remaining nucleic acid variants by at least one nucleotide. In particular embodiments, each of the barcodes includes at least 1-10 (e.g., 1-10, 1-20, 1-30, 1-40, 1-50, 1-100, or 1-500) nucleotides. In specific embodiments, at least two of the nucleotides of the barcode of each nucleic acid variant are located in consecutive codons. In alternative embodiments, at least two of the nucleotides of the barcode of each nucleic acid variant are not located in consecutive codons. In certain embodiments, the nucleotides of the barcodes of each nucleic acid variant are located within a portion of the nucleic acid variant including up to 10,000 contiguous nucleotides (e.g., up to 3, 4, 5, 6, 7, 8, 9, 10, 20, 30, 40, 50, 60 70, 80, 90, 100, 150, 200, 300, 400, 500, 600, 700, 800, 900, 1000, 2000, 3000, 4000, 5000, 6000, 7000, 8000, 9000, or 10,000 contiguous nucleotides).

In some embodiments of the twelfth and thirteenth aspects, the nucleic acid variants each include a double stranded nucleic acid. In particular embodiments, each of the identifier codons in a particular nucleic acid variant are located on the same strand of the double-stranded nucleic acid. In alternative embodiments, at least two of the identifier codons in a particular nucleic acid variant are located on different strands of the double-stranded nucleic acid. In certain embodiments, one of the identifier codons located on different strands can be identified by sequencing the opposite strand of the double-stranded nucleic acid. In specific embodiments, at least one of the identifier codons in each nucleic acid variant encodes leucine or serine. In certain embodiments, each of the nucleic acid variants further includes a check-sum codon.

In some embodiments of the twelfth and thirteenth aspects, each of the nucleic acid variants includes at least six identifier codons. In some embodiments, identical nucleic acid variants include identical barcodes. In alternative embodiments, identical nucleic acid variants include distinct barcodes. In certain embodiments, distinct nucleic acid variants include distinct barcodes.

In some embodiments of the twelfth and thirteenth aspects, the barcodes of one or more of the nucleic acid variants are identified by sequencing. In various embodiments, the sequencing produces a nucleic acid sequence read including the set of nucleotides occupying the wobble positions in the nucleic acid variants. In certain embodiments, the sequencing determines a nucleic acid sequence contig including the set of nucleotides occupying the wobble positions in the nucleic acid variants.

In some embodiments of the twelfth and thirteenth aspects, the barcodes of one or more of the nucleic acid variants are identified by single nucleotide polymorphism (SNP) genotyping.

In some embodiments of the twelfth and thirteenth aspects, each of the nucleic acid variants includes a nucleic acid sequence encoding a complementarity determining region (CDR). In particular embodiments, each of the nucleic acid variants includes nucleic acid sequences encoding two to six CDR regions. In some embodiments, each of the nucleic acid variants includes nucleic acid sequences encoding a CDR-H1, CDR-H2, and CDR-H3. In alternative embodiments, each of the nucleic acid variants includes nucleic acid sequences encoding a CDR-L1, CDR-L2, and CDR-L3. In further embodiments, each of the nucleic acid variants includes nucleic acid sequences encoding a CDR-H1, CDR-H2, CDR-H3, CDR-L1, CDR-L2, and CDR-L3. In specific embodiments, each of the nucleic acid variants includes a nucleic acid sequence encoding an scFv.

In some embodiments of the twelfth and thirteenth aspects, the library includes at least six nucleic acid variants. In particular embodiments, the library includes at least 100 nucleic acid variants. In further embodiments, the library includes at least 1000 nucleic acid variants. In other embodiments, the library includes between 1000-4096 nucleic acid variants. In specific embodiments, the library includes at least 10,000 nucleic acid variants. In certain embodiments, the library includes between 10,000-65,000 variants.

In some embodiments of the twelfth and thirteenth aspects, the positions of the identifier codons are invariant between the nucleic acid variants.

A fourteenth aspect of the present invention is a method of generating one or more polynucleotides encoding a desired complementarity determining region (CDR), the method including the steps of (a) providing a library of nucleic acid variants, each nucleic acid variant including a CDR-encoding nucleic acid sequence, (b) contacting the library with oligonucleotide primers, in which the oligonucleotide primers are capable of amplifying one or more desired CDR-encoding nucleic acid sequences from the library, (c) amplifying the one or more desired CDR-encoding nucleic acid sequences using the oligonucleotide primers, (d) contacting a support (e.g., a bead, chip, or surface) including one or more capture oligonucleotides to the amplified CDR-encoding nucleic acid sequences, such that a portion of each of the amplified CDR-encoding nucleic acid sequences is complementary to a portion of at least one of the capture oligonucleotides, thereby forming one or more capture complexes, (e) emulsifying the capture complexes in an emulsion medium, the emulsion medium further including reaction reagents sufficient to carry out an adjoining extension reaction, whereby the emulsion medium forms emulsion droplets, each emulsion droplet encapsulating about one of the capture complexes with the reaction reagents, and (f) incubating the emulsion droplet under conditions permitting adjoining extension of the amplified CDR-encoding nucleic acid sequences, thereby generating a polynucleotide encoding the desired CDR.

In some embodiments of the fourteenth aspect, the method further includes inserting the polynucleotide encoding the desired CDR into a framework, thereby generating a recombinant product, such that the recombinant product is capable of expressing a single-chain variable fragment antibody. In further embodiments, the method includes inserting the polynucleotide encoding the desired CDR into a framework, thereby generating a recombinant product, such the recombinant product is capable of expressing a functional immunoglobulin heavy chain and a functional immunoglobulin light chain, and the immunoglobulin heavy chain and the immunoglobulin light chain are capable of interacting to form a single functional binding moiety. In further embodiments, the method includes inserting the polynucleotide encoding the desired CDR into a framework, thereby generating a recombinant product, such that the recombinant product is capable of expressing a functional IgG binding moiety.

A fifteenth aspect of the present invention is a method of increasing the transformation efficiency of host cells for a nucleic acid of interest, the method including the steps of (a) contacting host cells with an excess amount of a nucleic acid of interest, the nucleic acid of interest lacking a predetermined restriction site, the host cells expressing a restriction enzyme that recognizes and cleaves the predetermined restriction site, and (b) culturing the host cells under conditions in which the restriction enzyme can cleave nucleic acids having the predetermined restriction site, thereby increasing the transformation efficiency of the host cells for the nucleic acid of interest.

In some embodiments of the fifteenth aspect, the nucleic acid of interest is in a mixture with other nucleic acids. In various embodiments, the restriction enzyme is expressed by the host cells. In specific embodiments, the restriction enzyme is expressed by a vector transformed into the host cells. In various embodiments, the host cells are bacteria. In preferred embodiments, the restriction enzyme is Eco29kI. In particular embodiments, the restriction enzyme is DpnI. In certain embodiments, the restriction enzyme is Sau3AI.

Definitions

"Binding moiety" means a protein or polypeptide, or a fragment thereof, capable of binding an antigen, such as an antigen displayed on the surface of a cell. A particular binding moiety is a cognate to an antigen if it is capable of binding a particular antigen or group of antigens. A cognate binding moiety and any antigen to which it binds is referred to as a "cognate pair." The binding of an antigen and cognate binding moiety is referred to as a "cognate pair interaction."

"Antibody" means any form of immunoglobulin, heavy chain antibody, light chain antibody, LRR-based antibody, or other protein scaffold with antibody-like properties, as well as any other immunological binding moiety known in the art, including antibody fragments (e.g., a Fab, Fab', Fab'2, F(ab')$_2$, Fd, Fv, Feb, scFv, or SMIP). The subunit structures and three-dimensional configurations of different classes of antibodies are known in the art.

"Antibody fragment" means a binding moiety that includes a portion derived from or having significant homology to an antibody, such as the antigen-binding portion of an antibody.

"Antigen," as used herein, can refer to any molecule or complex to which an affinity reagent (e.g., an antibody) can bind, or to which an affinity reagent (e.g., an antibody) can be generated against. Non-limiting examples of antigens include polypeptides (e.g., proteins), nucleic acids, lipids, and small molecules.

"Transgenic" means not endogenous to a host virion or cell. For example, a "transgenic protein" is not endogenous to the virion or cell by which it is encoded, expressed, or displayed.

"Fusion protein" means a protein or polypeptide that includes two polypeptide segments not naturally joined together. Fusion proteins of the present invention include an "antigen fusion protein," meaning a fusion protein that includes an antigen, as well as a "binding moiety fusion protein," meaning a fusion protein that includes a binding moiety.

"Cell surface" protein means a protein having at least one amino acid present on the external surface of a cell, such that a molecule contacted with the external surface of the cell may directly interact with the cell surface protein. A protein present on the cell surface may be referred to as "displayed."

"Viral surface" protein means a protein having at least one amino acid present on the external surface of a virus, such that a molecule contacted with the external surface of the virus may directly interact with the viral surface protein. A protein present on the viral surface may be referred to as "displayed."

"Recombination motif" means a nucleic acid sequence or domain that is capable of participating in a recombination event with a second nucleic acid sequence or domain. Two recombination motifs capable of participating in a recombination reaction with each other may be referred to as complementary. The recombination event may require additional reagents or specific conditions to occur. The recombination event may occur in a cell infected by a virion. For example, one of two nucleic acids containing complementary recombination motifs was present in the cell prior to infection, and one was present in the virion prior to infection. In some instances, the recombination event does not occur in the virion-infected cell, but rather, the two nucleic acids containing complementary recombination motifs are packaged into a new virion particle produced by the infected cell, such that when the new virion particle infects a second cell, the infected second cell induces the recombination event. "Recombination enzyme" means an enzyme or plurality of enzymes capable of facilitating recombination between complementary recombination motifs.

"Site-specific recombination motif" means a recombination motif capable of participating, in a sequence-dependent manner, in a recombination event with a second recombination motif having a particular pattern of nucleic acids. The site-specific recombination event may require additional reagents or specific conditions to occur.

"Attachment" means the binding of a virus to one or more proteins of a cell in a manner sufficient to allow infection of the cell. "Attachment-defective" means that a virus is reduced in its ability to bind to a cell as compared to a reference virus. An attachment-defective virus may be a virus that is unable to attach to a particular type of cell, a particular class of cells, or to all cells. Alternatively, an attachment-defective virus may be a virus that is reduced in its ability to bind to a particular type of cell, a particular class of cells, or to all cells. An attachment-defective virus may be capable of infecting a particular type of cell, a particular class of cells, or all cells under conditions that partially or completely rescue the attachment defect.

"Functional marker protein" means a protein that may be expressed within a cell and that may, upon expression, be detectable. A "functional marker gene" is a nucleic acid capable of expressing a functional marker protein. A "marker gene fragment" is a portion of a functional marker gene that is not itself detectable. In some instances, two marker gene fragments are required to form a functional marker gene.

"Functional marker complex" means a complex made up of two or more polypeptide subunits expressed within a cell that, when assembled as a complex, manifest one or more detectable phenotypes. Each subunit of a functional marker complex may be a protein or polypeptide that is not itself capable of detection. In some instances, a functional marker complex may have two subunits, such as two fusion protein subunits.

"Candidate cognate pair" means a candidate pair of a binding moiety and an antigen that may be tested to determine whether the binding moiety binds the antigen. An antigen and a binding moiety may be said to be tested if, for instance, the binding moiety and antigen are present within the same mixture or cell and incubated in a manner sufficient to allow binding. A binding moiety of one or more candidate cognate pairs may be an antibody or a non-antibody protein or polypeptide capable of binding an antigen. A binding moiety may be, e.g., a kinase, a phosphatase, a proteasomal protein, a protein chaperone, a receptor (e.g., an innate immune receptor or signaling molecule receptor), or any protein known in the art as a protein capable of participating in a protein-protein interaction. An antigen of one or more candidate cognate pairs may be any molecule capable of being bound by a binding moiety, including an immunogenic protein or polypeptide, natural protein or polypeptide, synthetic protein or polypeptide, enzymatically active protein or polypeptide, structural protein or polypeptide, as well as any other protein or polypeptide known in the art or that may be synthesized by one or more methods known in the art.

"Sequence" means either the order of amino acids in a protein or polypeptide or the order of nucleotides in a polynucleotide that encodes the protein or polypeptide.

"Flank" means that two oligonucleotides are capable of hybridizing to sequences found on opposite strands of a polynucleotide such that, were the oligonucleotides hybridized to the polynucleotide, the 3 terminus of each oligonucleotide would be oriented toward the 3' terminus of other. In this arrangement, the segment of the polynucleotide between the 5' termini of the oligonucleotides may be said to be flanked by the oligonucleotides. Two oligonucleotides that flank a segment of a polynucleotide may be referred to as a pair of oligonucleotides.

"Variable priming sequence" means a polynucleotide sequence that may serve as a hybridization site for an oligonucleotide and that includes one or more nucleotide positions that may be filled by any one of a plurality of distinct nucleotides.

By "wobble position" or "wobble base" is meant a nucleotide that can be changed without altering the amino acid encoded by the codon. "Wobble base" can further refer to a nucleotide or base located in a wobble position, or to the possible nucleotides that can occupy a particular wobble position without altering the encoded amino acid.

"Translationally-silent" or "translationally silent," as used herein, refers to a modification or mutation to a nucleic acid sequence that does not alter the amino acid(s) encoded by the nucleic acid sequence. For example, changing one or more wobble bases in a nucleic acid sequence can result in a distinct nucleic acid sequence that encodes the same amino acid sequence.

"Identifier codon," as used herein, means a codon containing one or more wobble positions that is used as part of a wobble base barcode. An identifier codon can include a single wobble position, e.g., at the third nucleotide of the codon. Alternatively, an identifier codon can have two or three wobble positions, which can include the first, second, or third nucleotides of the codon. A plurality of identifier codons can be located consecutively (e.g., forming a contiguous sequence). Alternatively, a plurality of identifier codons can be non-consecutive, for example, separated by at least one nucleotide (e.g., at least about 1, 2, 3, 4, 5, 10, 15, 20, 25, 30, 40, 50, 60, 70, 80, 90, 100, 125, 150, 200, 250, 300, 400, 500, 600, 700, 800, 900, 1000, 1500, 2000, 3000, 4000, or 5000 nucleotides). Multiple identifier codons can be located on the same strand of a double-stranded nucleic acid, or can be located on both strands of a double-stranded nucleic acid. A plurality of nucleic acid variants may all include identifier codons located at shared positions within their nucleic acid sequences, for example, within regions of the sequences that all encode an invariant amino acid sequence. Such a region may thus only vary in the nucleotides occupying the wobble positions of the identifier codons, such that each nucleic acid variant has a distinct wobble base barcode consisting of the nucleotides occupying the identifier codon wobble positions.

The terms "wobble base barcode" or "wobble barcode" refer to a barcode consisting of one or the combination of two or more wobble bases in a nucleic acid sequence. As used herein, the wobble base barcode itself only includes the set of nucleotides occupying the wobble positions.

By "excess amount" is meant a quantity of one reagent in stoichiometric excess to another reagent. For example, an excess amount of a nucleic acid relative to a number of host cells refers to a number of the nucleic acids exceeding the number of host cells, e.g., host cells to be transformed with the nucleic acid.

BRIEF DESCRIPTION OF THE DRAWINGS

FIG. 4 is a schematic showing a wobble barcode encoded into a nucleic acid construct encoding a complementarity-determining region (CDR), which can be used to identify and retrieve this particular CDR.

FIG. 8 is a schematic showing a strategy to select for recombination between plasmids. One vector contains the $Cm^R$ gene promoter, the initiating methionine (fMet) for the $Cm^R$ gene, and the phiC31 integrase attP site in frame with the fMet. A second vector contains the phiC31 attB site in frame with the $Cm^R$ gene. PhiC31 integrase-mediated recombination will generate the phiC31 integrase attR site in frame with the $Cm^R$ gene downstream of the promoter and fMet.

DETAILED DESCRIPTION

Figure 1:
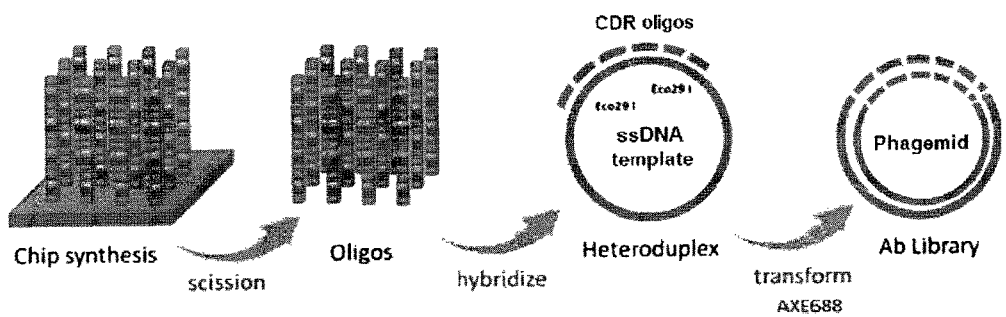
FIG. 1 is a schematic showing the construction of a CDR library from a gene chip to generate an antibody library.

The identification of binding moieties capable of selectively interacting with one or more target antigens is of scientific, medical, and commercial value. The present invention is directed toward the identification of such binding moieties. In some instances, the methods and compositions of the present invention are used to identify a plurality of distinct cognate binding moieties of each of a plurality of distinct antigens in a single reaction. A significant challenge in identifying binding moieties, and particularly in identifying binding moieties to multiple antigens in a single reaction, is the deconvolution of cognate pairs. The present methods include the use of one or more recombination motifs to enable the identification of cognate pairs: cognate pair formation allows isolation of a recombinant product including the sequence of an antigen and a cognate binding moiety of the antigen. The invention also features compositions and methods for wobble base barcoding of nucleic acid molecules, for example, recombinant cognate pairs, antibody libraries, CDR libraries of the present invention. Moreover, the invention provides methods for producing such libraries, and for increasing transformation efficiency and recombinant rate.

The present invention broadly encompasses bringing two nucleic acid elements together within a single compartment (e.g., a cell) and allowing a recombination event to occur that fuses the two nucleic acid elements. Fusion of the two nucleic acid elements can involve, for example, any fusing agent known in the art (e.g., chemical, protein, or lipid fusion agents and/or agents that can be activated by, e.g., heat or light). The invention includes at least two distinct methods by which one or more recombination motifs may be used to identify one or more cognate pairs. In at least a first method of the invention, an antigen displayed by a cell is bound by a cognate binding moiety displayed by a virus, resulting in selective delivery of a viral nucleic acid encoding the binding moiety into the cell; subsequent recombination of the viral nucleic acid encoding the binding moiety and a cellular nucleic acid encoding the antigen results in a single recombinant product that includes the sequence of each. In at least a second method of the invention, two vectors, one encoding a binding moiety fusion protein and the other encoding an antigen fusion protein, are transferred into a single cell, in which the two fusion proteins may be expressed and the two vectors may recombine; cognate pair interaction between the binding moiety and the antigen results in the formation of a functional complex capable of marking a cell in a detectable manner, after which cognate pairs may be identified from the recombinant products of marked cells.

In further methods of the invention, an antigen on a cell may be capable of binding to a cognate binding moiety on, e.g., another cell. Thus, the methods of the invention can further include transferring a nucleic acid element from one cell to another upon binding of cell surface moieties on the two cells. Transfer of nucleic acid elements from one cell to another can be prevented until a desired event occurs. For example, male (F+) and female (F−) *E. coli* cells can be used, such that mating of F+ and F− cells results in transfer of the nucleic acid element from the F+ cell to the F− cell. In further instances, a sperm and egg or a cell and an intracellular pathogen capable of infecting the cell (e.g., a dicotylendous plant and a *Agrobacterium tumafaciens* pathogen) can be used.

Alternatively, a haploid cell can be mated with another haploid cell in the methods of the invention, for example, to form a diploid daughter cell containing genetic elements (e.g., nucleic acids including complementary recombination motifs) from both parent haploid cells. For example, yeast mating types a and alpha can be used. For example, a yeast of mating type alpha can be crossed to a yeast of mating type a strain, in which the protein required for mating on the surface of the yeast is repressed in one or the other yeast mating type. The two yeasts can each display one of two binding partners (e.g., one yeast displays a Fab library on its surface, and the second yeast displays the antigen on its surface). Binding of the two binding partners can then be allowed to occur, followed, e.g., by washing the cells and, e.g., inducing the factor required for mating in one or both yeasts. Mating can then occur, resulting in a diploid cell containing the two nucleic acids from each of the original yeast cells, each of the nucleic acids containing the genes for one of the binding partners. The two nucleic acids can further include complementary recombination motifs, such that recombination can occur between the two nucleic acids. Recombination can further induce an identifier phenotype as described herein (e.g., expression of a selectable or differentiable marker). Thus, the binding partners (e.g., Fab and antigen) can be identified in the resultant recombinant product.

The present methods may be applicable, e.g., in screens to identify medically, commercially, or industrially relevant binding moieties.

Selective Infection of Antigen-Displaying Cells by Binding Moiety-Displaying Virions In some methods of the present invention, a cell displaying a particular antigen is selectively infected by a virion displaying a cognate binding moiety. In particular embodiments, the virion is an attachment-defective virion. In these embodiments, cognate pair interaction between an antigen displayed by a cell and a binding moiety displayed by a virion may rescue the attachment defect, allowing selective infection. In particular embodiments, a virion is only or selectively able to infect a cell if the virion displays a cognate binding moiety of an antigen displayed by the cell and the pair bind in a manner sufficient to rescue the attachment defect.

Cells

A cell of the present invention may be any manipulable cell known in the art, such as a cell descending from a laboratory, commercial, or industrial cell line known in the art. The cell may be an archaeal cell, bacterial cell, fungal cell, or eukaryotic cell. The cell may be a yeast cell, plant cell, or animal cell. In some instances, the cell may be an *E. coli* cell, *S. cerevisiae* cell, or animal cell. The cell may be, e.g., a mammalian cell such as a human cell. The cell may be an immortalized cell. Alternatively, the animal cell may be a non-immortalized cell. A cell of the present invention may display an antigen.

Antigens

An antigen of the present invention may be any molecule to which a binding moiety may bind. For example, an antigen can be a polypeptide (e.g., a protein), nucleic acid, small molecule, or lipid. An antigen of the present invention may be displayed on the surface of a cell (e.g., a cell surface protein). In some instances, an antigen of the present invention is a protein or polypeptide that is normally found on the surface of a cell. In some instances, an antigen is transgenic. In other instances, the antigen includes a protein or polypeptide that is not normally found on the surface of a cell. In certain instances, the antigen is a protein or polypeptide that is normally found within a cell, such as in the cytoplasm or an organelle. In certain instances, the antigen is a transgenic protein or polypeptide. In certain instances, the antigen is a lipid (e.g., a modified lipid) and the binding moiety is a lipid ligase.

An antigen may be any natural or synthetic protein, e.g., a protein known in the art. An antigen may be a protein or peptide found in a protein or peptide database (e.g., SWISS-PROT, TrEMBL, SBASE, PFAM, or others known in the art), or a fragment or variant thereof. An antigen may be a protein or peptide that may be derived (e.g., by transcription and/or translation) from a nucleic acid sequence known in the art, such as a nucleic acid sequence found in a nucleic acid database (e.g., GenBank, TIGR, or others known in the art) or a fragment or variant thereof.

An antigen may be a protein or polypeptide endogenous to a pathogen, such as a protein or polypeptide selectively expressed or displayed by one or more cells of a pathogen. The pathogen may be, e.g., a virus, infectious bacteria, infectious fungus, or infectious eukaryote. For example, the pathogen may be *Burkholderia pseudomallei*. In some instances, the pathogen is a pathogen of one or more animal species, such as humans. Numerous pathogens are known in the art. In particular embodiments, a plurality of distinct antigens of the present invention is selected from a single pathogen. In particular embodiments, a plurality of distinct antigens of the present invention are selected from a plurality of distinct pathogens.

An antigen may be a protein or polypeptide associated with diseased cells or a disease state. For instance, an antigen may be a protein or polypeptide associated with cancer cells, such as a protein or polypeptide selectively expressed by cancer cells. In certain instances, the antigen is a tumor marker, i.e., a substance produced by a tumor or produced by a non-cancer cell in response to the presence of a tumor. Many tumor markers are not exclusively expressed by cancer cells, but may be expressed at elevated levels in cancerous cells or expressed at elevated levels in non-cancer cells in response to the presence of a tumor. The antigen may be a protein or polypeptide expressed in connection with any disease or condition known in the art.

An antigen may be a commercially valuable product, such as a protein or polypeptide for use in the treatment of a disease or disorder or useful as a research tool. In such instances, a cognate binding moiety of the antigen may be useful in the isolation of the antigen, e.g., for research or commercial purposes.

An antigen of the present invention may include one or more modified amino acids, such as a post-translationally modified amino acid. For example, one or more amino acids of an antigen of the present invention may be glycosylated, acetylated, amidated, formylated, gamma-carboxyglutamic acid hydroxylated, methylated, phosphorylated, sulfated, or modified with pyrrolidone carboxylic acid. An antigen amino acid may include one or more amino acids having a phosphoserine. An antigen of the present invention may include one or more amino acids having a phosphothreonine or phosphotyrosine modification.

The present invention may be applicable to any antigen protein or polypeptide that may be displayed on the surface of a cell. An antigen may be encoded by the cell on which it is displayed. In some instances, the antigen may be present in an antigen fusion protein.

In some instances, multiple distinct antigens can be displayed on the surface of a cell. In certain instances, each of the distinct antigens can be encoded by a nucleic acid sequence within the cell, which can, e.g., be barcoded. In some instances, multiple distinct binding moieties can be permitted to bind to antigens on a cell, and nucleic acids encoding the multiple distinct bind moieties transduced into the cell and attached to a nucleic acid encoding the bound antigen, e.g., to form cognate pairs according to the methods of the present invention. The cell may also include a barcode identifying the cell of origin for the antigens. In some instances, the methods of the invention can be multiplexed, for example, by internally barcoding a plurality of cells and attaching antigens to the surface of each cell. For example, a plurality of cells (e.g., $E.$ $coli$ cells) can be induced to express neutravidin on their cell surfaces, followed by binding of a plurality (e.g., 1000) distinct biotinylated small molecules to the cell surfaces.

Viruses

A virus of the present invention may be any manipulable virus known in the art, e.g., for laboratory, commercial, or industrial use. A virus of the present invention may be a virus known to be capable of infecting archaea, fungi, bacteria, or eukaryotes. A virus may be capable of infecting plants or animals. In some instances, the virus may be a virus known to infect $E.$ $coli$ cells or yeast cells. A virus may be a dsDNA virus, ssDNA virus, dsRNA virus, ssRNA virus, ssRNA-RT virus, or dsDNA-RT virus. For example, the virus may be a lentivirus, adenovirus, adeno-associated virus, baculovirus, measles virus, influenza virus, human immunodeficiency virus (HIV), arbovirus, cholera virus, chicken pox virus, dengue virus, diphtheria virus, hantavirus, herpes virus, Ebola virus, Marburg virus, parainfluenza virus, rabies virus, syphilis virus, bacteriophage, lambda bacteriophage, cytomegalovirus, Epstein Barr Virus (EBV), vaccinia virus, or other virus known in the art. A virus of the present invention may be, e.g., M13 bacteriophage. In certain instances, a virus can be baculovirus and the cell to be infected by the virus can be a mammalian cell. A virus of the present invention may further be a variant of a form known in the art.

A reaction of the present experiment may include one or more virus types and one or more types of cells. In such embodiments, the viruses and cells may be selected so that each virus type is capable of infecting one or more of the included types of cells. A virion of the present invention may display a binding moiety. In some instances, a virus can display a plurality of distinct binding moieties. In certain instances, the distinct binding moieties are encoded by nucleic acid sequences in the virus (e.g., barcoded nucleic acid sequences) that can, for example, be transferred to the cell upon viral infection of the cell and attached to nucleic acids encoding the cognate antigens bound by each binding moiety, e.g., to form cognate pairs according to the methods of the invention.

Attachment Defects

A virus may attach to a cell in a manner sufficient to allow infection of the cell if a protein or peptide displayed by the virus is capable of binding a protein or peptide displayed by the cell. A virus that does not display a protein or peptide capable of binding a protein or peptide displayed by the cell is attachment defective. An attachment defect of the invention may be an inherent, endogenous, mutant, or engineered characteristic that reduces the ability of a virus to infect a particular type of cell, a particular class of cells, or to all cells. In embodiments including an attachment-defective virus, each attachment defective virion may display a binding moiety of the present invention. Binding of a virally displayed binding moiety to a cell-displayed antigen may rescue the attachment defect, allowing the virion to infect the cell. An attachment-defective virus of the present invention may be, e.g., Gp3-defective M13 bacteriophage. In certain instances, an attachment-defect may be the result of species incompatibility; i.e., cells present in a reaction of the present invention are of a species that the virus is not naturally able to infect.

A reaction of the present invention may include one or more types of attachment-defective virus and one or more types of cells. In such embodiments, the viruses and cells may be selected so that each type of virus is capable of infecting one or more of the included cell types upon rescue of the attachment defect, e.g., by a cognate pair interaction.

Infection Defects

In some embodiments of the present invention, a virion attaches to a cell but fails to infect the cell due to the absence of one or more proteins that contribute to the process of infection. One or more proteins, peptides, molecules, or other moieties that contribute to the process of infection can be referred to as an infection apparatus. In some instances, an infection apparatus is displayed by a cell or included in a cell. In particular embodiments, an infection defect of one or more cells with respect to one or more particular virions is condition-dependent. Condition-dependent infection defect means that under certain non-permissive incubation conditions, a virion capable of attaching to a cell will be incapable of infecting that cell, while under other, permissive incubation conditions, the virion will be capable of both attaching to and infecting the cell. A condition-dependent infection defect may be, e.g., a temperature-sensitive or transcription activator-sensitive infection defect. For instance, in certain embodiments, a cell displays an infection apparatus capable of mediating infection by a particular virion only when incubated at a temperature regimen sufficient to allow expression of the infection apparatus. In other instances, the infection apparatus is an internal cellular component, i.e. a component that is not displayed. In particular examples, the cell is an $E.$ $coli$ cell and the virion is an M13 bacteriophage. In certain embodiments, the $E.$ $coli$ cell displays the F pilus when incubated at 37° C., but not when incubated at 16° C. Temperature-sensitive F pilus constructs and their uses are known in the art, e.g., in Benhar et al. 2000 *JMB* 301: 893-904, which is herein incorporated by reference.

In other embodiments, the cell expresses an infection apparatus only when incubated with sufficient activator molecules to induce sensitive elements or promoters of said apparatus. For instance, a conditional infection defect designed to identify cognate pairs may involve the recombinant expression of the F pilin protein under control of a promoter response element. In particular examples, the activator molecules of the response element may be antibiotics, e.g., tetracyclines. In certain embodiments, the cell displays the F pilus when incubated with tetracyclines or other activator molecules, but not when incubated without activator molecules. Under permissive incubation conditions with the activator molecule, the virion will be capable of attaching to and infecting the cell. In some instances, the cell is an *E. coli* and the virion is an M13 bacteriophage. Tetracycline-responsive promoters and their uses are known in the art, e.g., Loew et al., 2010 *BMC Biotechnol* 10:81.

In some embodiments, close proximity can be used to facilitate infection. For example, a targeting moiety present on a virus may have a cognate moiety on a cell surface (e.g., genetically expressed by the cell or physically attached to the cell). Preferably, the viral targeting moiety and the cellular cognate moiety can bind to each other with high affinity. Thus, binding of the viral targeting moiety and cellular cognate moiety can bring the virus and cell into close enough proximity to facilitate binding of a binding moiety on the virus to a cognate antigen on the cell according to the methods of the invention. The viral targeting moiety may or may not be a binding moiety of the invention. The cellular cognate moiety may or may not be a cognate antigen of the cell.

In some embodiments, rescue of a condition-dependent infection defect may involve the transfer of one or more genetic elements into a cell that does not express the infection apparatus. A transducing phage may contain a genetic element encoding the infection apparatus. In some instances, the element may encode a protein or polypeptide of the F pilus. In particular examples, the cell may be *E. coli* and the transfer of genetic material into the cell may be mediated by phage known to infect *E. coli*. The virus may be a bacteriophage, lambda bacteriophage, M13 phage, or other phage known in the art. Upon infection of the cell with the phage, recombination may result in the integration of the F pilus element into the cellular nucleic acid. In some instances, recombinant expression of the element may allow display of the infection apparatus. Phage transfection may be performed before or after emulsion, as described herein, and prior to recombination.

In some embodiments in which a cell displays an antigen and a virion displays a cognate binding moiety, the antigen and cognate binding moiety bind under conditions under which the cell is infection defective, i.e., under non-permissive conditions. A subsequent shift to a permissive condition may then allow the virion to infect the cell. The shift to permissive conditions rescues the infection defect. In particular embodiments, a virion bound to an infection-defective cell under non-permissive conditions is separated from the cell prior to infection of the cell by the virion under permissive conditions. In still more particular conditions, a cleavage reagent separates the virion from the cell prior to infection. In certain embodiments, e.g., embodiments in which a cell displaying an antigen is separated from a virion displaying a cognate binding moiety prior to infection, e.g., by stochastic separation or enzymatic cleavage, virion-bound cells are emulsified such that the separated virion proceeds to infect the cell to which it was previously bound. In certain embodiments, a cell is infection defective, a virion is attachment-defective, or both. Each droplet of the emulsion may include 0-10 cells, such as, on average, 0-2 cells. In particular embodiments, droplets of an emulsion may include less than 1 cell, such as, e.g., 0.1, 0.2, 0.3, 0.4, 0.5, 0.6, 0.7, 0.8, 0.9, or 0.99 cells, 1 cell, or 1-2 cells, such as, e.g., 1, 1.1, 1.2, 1.3, 1.4, 1.5, 1.6, 1.7, 1.8, 1.9, or 2 cells.

In certain embodiments, the emulsion or droplets present in the emulsion further include a protease capable of cleaving one or both of one or more antigens or one or more bound cognate binding moieties, e.g., by a displayed cleavage site included in the antigen or binding moiety fusion proteins. Alternatively, the protease can be target non-specific. In particular embodiments, the emulsion includes TET protease. In other embodiments, the emulsion includes a TEV protease. In such embodiments, a TEV cleavage site may be placed between displayed binding moiety, e.g., an scFv, and a protein from which it is displayed, e.g., Gp3. The emulsion is incubated in a manner sufficient to allow cleavage of one or more displayed antigens or one or more displayed cognate binding moieties.

In any of the above embodiments in which one or more cells are infection-defective, a reaction including cells displaying antigens and virions displaying binding moieties, having been incubated in a manner sufficient to allow binding of one or more antigens by one or more cognate binding moieties but not sufficient to rescue the infection defect, may be washed one or more times. A wash step may purify one or more cells from one or more unbound virions. A wash step may include incubation under conditions that allow separation of one or more bound virions from the cell to which each was bound. In particular embodiments, a wash step will include incubation under conditions that allow separation of one or more bound virions from the cell to which each was bound while allowing one or more other bound virions to remain bound. A wash step may result in a waste product including one or more virions or one or more cells having been present in the reaction prior to the wash step. The waste product may be discarded, while the remainder may be optionally treated with one or more additional wash steps. The remainder may be incubated in a manner sufficient to allow rescue of the infection defect, e.g., after subsequent compartmentalization, e.g., emulsification. Suitable wash steps are known in the art. A particular embodiment may include 1, 2, 3, 4, 5 or more wash steps.

A particular method of utilizing a conditional infection defect to identify cognate pairs is referred to as delayed infectivity panning (DIP). DIP is an approach for the in vivo isolation of interacting protein pairs. In DIP an antigen is displayed in many copies on the surface of F⁺ *E. coli* cells by fusion to Lpp-OmpA. To prevent premature, non-specific infection by phage, the cells are rendered functionally F⁻ by growth at 16° C. The antigen-displaying cells capture binding moiety-displaying phage by cognate pair interaction. Following removal of unbound phage by washing, infection of the cells by bound phage is initiated by raising the temperature to 37° C., facilitating F pilus expression. The phage then dissociate from the antigen and infect the bacteria through the F pilus. Benhar et al. 2000 (*JMB* 301: 893-904) demonstrate significant enrichment of target-specific binding moieties in a single DIP cycle. The effectiveness of DIP makes it suitable, e.g., for the isolation of rare clones present in large libraries or the rapid isolation and characterization of binding moieties in numerous protein-protein interactions. In particular embodiments, the methods of the present invention further include the step of emulsifying bound cells after the washing step and prior to the step of raising the temperature.

A reaction of the present invention may include one or more types of virus and one or more types of infection-defective cells. In such embodiments, the viruses and cells may be selected so that each type of virus is capable of infecting one or more of the included cell types upon rescue of the infection defect(s), e.g., by incubation under permissive conditions. One of skill in the art will recognize that, in embodiments involving one or more cells having a temperature-sensitive infection defect, temperature conditions other than those specifically stated herein may constitute a non-permissive condition and a permissive condition. In certain embodiments, one or more of the virions are attachment defective and one or more of the cells are conditionally infection defective. In particular embodiments, one or more virions are not attachment-defective and the cells are conditionally infection defective.

Binding Moieties

A binding moiety of the present invention may be any protein or polypeptide capable of binding an antigen. In some instances, a binding moiety of the present invention includes a protein or polypeptide that is normally found on the surface of a virus. In some instances, a binding moiety is a transgenic binding moiety. In some instances, a binding moiety is an antibody, such as a whole antibody or an antibody fragment, such as an antigen-binding fragment.

An antibody of the present invention may be a whole antibody or immunoglobulin or an antibody fragment. An antibody may be multispecific, e.g., bispecific. An antibody of the present invention may be mammalian (e.g., human or mouse), humanized, chimeric, recombinant, synthetically produced, or naturally isolated.

In most mammals, including humans, whole antibodies have at least two heavy (H) chains and two light (L) chains connected by disulfide bonds. Each heavy chain consists of a heavy chain variable region ($V_H$) and a heavy chain constant region ($C_H$). The heavy chain constant region consists of three domains, $C_H1$, $C_H2$, and $C_H3$ and a hinge region between $C_H1$ and $C_H2$. Each light chain consists of a light chain variable region ($V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Antibodies of the present invention include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

An antibody fragment of the present invention may include one or more segments derived from an antibody. A segment derived from an antibody may retain the ability to specifically bind to a particular antigen. An antibody fragment may be, e.g., a Fab, Fab', Fab'2, F(ab')$_2$, Fd, Fv, Feb, scFv, or SMIP. An antibody fragment may be, e.g., a diabody, triabody, affibody, nanobody, aptamer, domain antibody, linear antibody, single-chain antibody, or multispecific antibodies formed from antibody fragments.

Examples of antibody fragments include: (i) a Fab fragment: a monovalent fragment consisting of $V_L$, $V_H$, $C_L$, and $C_H1$ domains; (ii) a F(ab')$_2$ fragment: a bivalent fragment comprising two Fab fragments linked by a disulfide bridge at the hinge region; (iii) a Fd fragment: a fragment consisting of $V_H$ and $C_H1$ domains; (iv) a Fv fragment: a fragment consisting of the $V_L$ and $V_H$ domains of a single arm of an antibody; (v) a dAb fragment: a fragment including $V_H$ and $V_L$ domains; (vi) a dAb fragment: a fragment consisting of a $V_H$ domain; (vii) a dAb fragment: a fragment consisting of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, e.g., by a synthetic linker that enables them to be made as a single protein chain in which the $V_L$ and $V_H$ regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, e.g., by genetic engineering. A chimeric antibody may include immunoglobulin gene segments belonging to different species (e.g., from a mouse and a human).

An antibody of the present invention may be a human antibody. A human antibody refers to a binding moiety having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, e.g., mutations. A variation or additional amino acid may be introduced, e.g., by human manipulation. A human antibody of the present invention is not chimeric.

An antibody of the present invention may be humanized, meaning that an antibody that includes one or more complementarity determining regions (e.g., at least one CDR) substantially derived from a non-human immunoglobulin or antibody is manipulated to include at least one immunoglobulin domain having a variable region that includes a variable framework region substantially derived from a human immunoglobulin or antibody.

In particular embodiments, one or more binding moieties of the present invention is an antibody derived from the sequence of an antibody expressed by a (e.g., a B-cell) cell of an inoculated subject. In particular embodiments, one or more binding moieties of the present invention is an antibody derived from the sequence of an antibody expressed by a naïve cell.

In certain embodiments of the present invention, a binding moiety is based on an alternative scaffold. Scaffolds based on different human or non-human proteins or protein domains are known in the art (see, e.g., Gebauer, M. & Skerra, A. *Curr. Opin. Chem. Biol.* 2009, 13:245-255). Different proteins have been investigated as frameworks, including affibodies, lipocalins, ankyrin-repeat proteins, natural peptide binding domains, enzymes, GFP, small disulfide-bonded peptides, protease inhibitors, and others.

A binding moiety of the present invention may be a protein or polypeptide that is not an antibody. A binding moiety may be, e.g., a kinase, a phosphatase, a proteasomal protein, a protein chaperone, a receptor (e.g., an innate immune receptor or signaling peptide receptor), a synbody, an artificial antibody, a protein having a thioredoxin fold (e.g., a disulfide isomerase, DsbA, glutaredoxin, glutathione S-transferase, calsequestrin, glutathione peroxidase, or glutathione peroxiredoxin), a protein having a fold derived from a thioredoxin fold, a repeat protein, a protein known to participate in a protein complex, a protein known in the art as a protein capable of participating in a protein-protein interaction, or any variant thereof (e.g., a variant that modifies the structure or binding properties thereof). A binding moiety of the present invention may be any protein or polypeptide having a protein binding domain known in the art, including any natural or synthetic protein that includes a protein binding domain. A binding moiety of the present invention may also be any protein or polypeptide having a polynucleotide binding domain known in the art, including any natural or synthetic protein that includes a polynucleotide binding domain.

In any embodiment of the present invention, a population of binding moiety-displaying virions may be subtracted prior to being contacted with cells displaying antigens of the present invention. For instance, a population of scFv-displaying M13 bacteriophage can be subtracted against F− *E. coli* cells that do not display binding moieties of the present invention to remove non-specific binding moieties and binding moieties that bind non-target epitopes displayed by F− *E. coli* cells. In other examples, a population of scFv-displaying M13 bacteriophage is subtracted against F+*E. coli* cells that do not display binding moieties of the present invention to remove non-specific binding moieties and binding moieties that bind non-target epitopes displayed by F+*E. coli* cells. In certain embodiments, a population of binding moiety-displaying virions is subtracted through two or more rounds of subtraction. For example, in particular embodiments, an M13 bacteriophage scFv library is subtracted against F− *E. coli* cells and subsequently subtracted against F+*E. coli* cells. Methods of subtraction are known in the art.

Fusion Proteins

An antigen or binding moiety of the present invention may be present in a fusion protein that enables display. In some instances, a binding moiety is present in a binding moiety fusion protein that further includes a segment that enables viral display. In some instances, an antigen is present in a binding moiety fusion protein that further includes a segment that enables cell surface display. A segment that enables display may be any polypeptide including a sequence of a known transmembrane domain or a sequence derived therefrom.

In one example, an antigen is fused to an F pilin protein (e.g., TraA) or a fragment thereof for expression on the surface of a bacterial cell, e.g., an *E. coli* cell. In particular instances, the fusion protein includes a segment without which the antigen would not be displayed.

In another example, an antigen is fused to the outer membrane protein OmpA or a fragment thereof. Such a fusion protein may further include one or more amino acids derived from the major outer membrane protein Lpp. In particular instances, expression of a fusion protein including Lpp-OmpA and an antigen in *E. coli* cells results in display of the antigen. Lpp-OmpA fusion constructs are known in the art, e.g., in Benhar et al. 2000 *JMB* 301: 893-904, which is herein incorporated by reference.

In particular embodiments in which *E. coli* cells that conditionally express the F pilus are contacted with binding moiety-displaying phage, e.g., M13 bacteriophage, the antigen fusion protein will not include an F pilus protein, e.g., TraA.

Not all displayed antigens or displayed binding moieties of the present invention are fusion proteins.

Recombination Motifs

A virion or cell of the present invention may include a nucleic acid encoding a binding moiety or antigen, respectively. A nucleic acid encoding an antigen or binding moiety may further include one or more recombination motifs. A recombination motif may be from 20 to 500 or more nucleotides in length, such as 20, 30, 40, 50, 100, 200, 300, 400, or 500 or more nucleotides. Recombination may occur, for example, between two DNA molecules, a DNA molecule and an RNA molecule, or two RNA molecules. Recombination between a nucleic acid encoding an antigen and a nucleic acid encoding a binding moiety may occur when one or both includes a recombination motif.

A segment of a nucleic acid with which a recombination motif may participate in a recombination event may be referred to as a complementary recombination motif. For certain recombination motifs, recombination does not depend upon the sequence of a complementary recombination motif, i.e., there is no significant limitation regarding the sequence of a complementary recombination motif. Certain other recombination motifs selectively participate in recombination with complementary recombination motifs having a particular sequence or particular sequence characteristics. Such recombination motifs are referred to as site-specific recombination motifs. In some instances, a recombination motif may be divided, having two or more regions with particular sequence requirements separated by one or more sequences that are not substantially constrained and/or do not directly participate in recombination.

In some instances, complementary recombination motifs are identical. In other instances, complementary recombination motifs are non-identical. In some instances, all of the nucleotides comprising a site-specific recombination motif may be defined. In other instances, only a subset of the nucleotides comprising a site-specific recombination motif may be defined, such as 5%, 10%, 15%, 20%, 25%, 50%, 60%, 70%, 80%, 90%, 95%, 99%, or 99.5% of nucleotides present in the site-specific recombination motif. Complementary recombination motifs may include, e.g., a phage motif, a bacterial motif, or a direct repeat motif.

Recombination motifs that are not substantially site-specific are known in the art. Examples of recombination systems that are not substantially site-specific may include particular mechanisms of transposition.

Various sets of complementary recombination motifs are known in the art. For example, a pair of complementary recombination motifs may include an attP motif and an attB motif. In a second example, a pair of complementary recombination motifs may include a hixL motif and hixR motif.

Other examples of site-specific recombination motifs include the Tn7 site-specific attTn7 motif. Other examples are known in the art.

In certain instances, the sequence of a recombination motif will be translated in a single polypeptide including the translated recombination motif and a marker protein, binding moiety, or antigen. For instance, the attR site having the sequence 5'-ccccaactggggtaacctttgggctcccggcgcgtac-3'- (SEQ ID NO: 26) can be translated in 5 reading frames that do not contain a stop codon (PNWGNLWAPRAR (SEQ ID NO: 27), PTGVTFGLPGRV (SEQ ID NO: 28), VRARGAQRLPQLG (SEQ ID NO: 29), YAPGEPKGYPSW (SEQ ID NO: 30), and TRPGSPKVTPVG (SEQ ID NO: 31)) as well as a $6^{th}$ reading frame that does contain a stop codon.

Recombination Enzymes

Additional reagents or particular conditions may be required to facilitate recombination between complementary recombination motifs. In some instances, recombination requires a recombination enzyme. A recombination enzyme may be a recombinase. A recombination enzyme may be an integrase. A recombination enzyme may be, e.g., a serine family recombinase or tyrosine family recombinase. The serine and tyrosine recombinase families are each named according to the conserved nucleophilic amino acid that interacts with DNA during recombination. Serine family recombinases include HIN invertase, which recognizes hix sites, and Tn3 resolvase. Tyrosine family recombinases included lambda integrase, which recognizes att sites, Cre, which recognizes/ox sites, and FLP, which recognizes frt sites. Other recombination enzymes are known in the art. For the purposes of the present invention, a recombination enzyme capable of facilitating recombination of complementary recombination motifs present in a given reaction may be selected.

Marker Genes and Marker Gene Fragments

Infection of a cell by a virion may result in expression of a functional marker protein from a marker gene, the expression of which may directly or indirectly result in a detectable phenotype. The detectable phenotype may be used to select or isolate one or more infected cells.

The functional marker protein may include a promoter such that expression of the functional marker protein may be driven by a protein expressed by the infected cell. Alternatively, the promoter of the functional marker gene may be such that expression of the functional marker protein may be driven by a protein introduced to the cell upon infection. In some instances, the functional marker gene is induced or enhanced, directly or indirectly, by one or more stimuli, such as a change in reaction temperature, addition of a metabolite to the reaction, addition of a small molecule to the reaction, or addition of an enzyme to the reaction. Inducible expression systems are known in the art.

In some instances, expression is modulated by codon optimization or other cell-type specific mechanisms. Methods of expressing proteins in various cell types of the present invention are known in the art.

Examples of detectable phenotypes include, without limitation, luminescence, fluorescence, antibiotic resistance, toxin resistance, altered growth rate, altered response to an analyte, altered cell structure, altered colony formation, altered auxotrophy, resistance to light (e.g., resistance to UV light), increased thermal resistance, resistance to viral particles, resistance to low pH, resistance to high pH, or salt tolerance. Additional detectable phenotypes (e.g., resistance or tolerance to further biophysical phenomena and/or biochemical reagents) that may be linked to the expression of a gene are known in the art. Further, genes capable of manifesting these detectable phenotypes are known in the art. For example, a detectable phenotype may result from expression of green fluorescent protein (e.g., gfp), red fluorescent protein (e.g., rfp), yellow fluorescent protein (e.g., yfp), an ampicillin resistance gene (amp), a tetracycline resistance gene (tet), a kanamycin resistance gene (kan), beta galactosidase (β-gal), an alanine synthesis gene (e.g., argA), a cystein synthesis gene (e.g., cysE), a leucine synthesis gene (e.g., lysA), a threonine synthesis gene (e.g., thrC), and many others known in the art. Alternatively, the functional marker protein may be a gene that directs or contributes to the expression of a gene that manifests a detectable phenotype. Further still, methods for selecting or isolating cells having a detectable phenotype are known in the art. Selecting or isolating one or more cells having a phenotype resulting from expression of a functional marker protein may include, depending upon the detectable phenotype, flow cytometry, culturing a population of cells in the presence of the relevant antibiotic or toxin, culturing a population of cells in the absence of a particular organic compound, or microscopy techniques. Additional methods of selecting and isolating cells having particular detectable phenotypes are known in the art.

Expression of a functional marker protein may require recombination between a first nucleic acid and a second nucleic acid, such as a viral nucleic acid and a cellular nucleic acid. In such embodiments, the marker protein may be divided into a first marker gene fragment and a second marker gene fragment. In certain embodiments, the first and second nucleic acids may respectively include corresponding complementary recombination motifs. In particular, the first and second nucleic acids may respectively include corresponding site-specific recombination motifs.

When a functional marker gene has been divided into two distinct marker gene fragments, the functional marker gene may be divided such that each fragment is independently incapable of producing a functional marker protein. For instance, the two marker gene fragments may be a promoter and a coding region, respectively. For instance, one marker gene fragment may include only a promoter, and no nucleotides encoding the functional marker protein to be expressed from the functional marker gene, while the other marker gene fragment includes the entire coding region of the functional marker gene. In other embodiments, one fragment comprises the promoter and all or part of one or more exons of a functional marker gene, and a second fragment comprises the remaining all or part of one or more exons of a functional marker gene. For instance, one marker gene fragment may include the promoter of a functional marker gene and all or part of one or more 5 exons of the functional marker gene, while the other marker gene fragment includes the remaining 3' nucleotides of the functional marker gene. In particular embodiments, the division of a first and second marker gene fragment may occur within an intron of a functional marker gene sequence. A fragment of a functional marker gene that includes all or a portion of the promoter region of a functional marker gene may be referred to as a promoter fragment. A fragment of a functional marker gene that includes all or a portion of the coding region of a functional marker gene may be referred to as a coding fragment.

In embodiments in which a functional marker gene is divided into two marker gene fragments encoded by nucleic acids having site-specific recombination motifs, the first marker gene fragment and second marker gene fragment may be positioned such that recombination between the first and second recombination motifs may be predicted to result in the formation of a functional marker gene capable of expression a functional marker protein in a cell. For instance, a first marker gene encoded by a first nucleic acid may be adjacent to a first site-specific recombination motif present on the first nucleic acid and a second gene encoded by a second nucleic acid may be adjacent to a second site-specific recombination motif present on the second nucleic acid. A marker gene fragment will be said to be adjacent to a site specific recombination motif if it is positioned in the proximity of the recombination motif such that any nucleotides intervening between the marker gene and the recombination motif, if any, will not preclude expression of a functional marker gene upon recombination. A marker gene adjacent to a recombination motif may be adjacent or separated, e.g., by 1 to 200 or more nucleotides, such as 1, 5, 10, 25, 50, 75, 100, 150, or 200 or more nucleotides. In certain embodiments, a marker gene fragment and a recombination motif may be separated, e.g., by 201, 400, 600, 800, or 1,000 nucleotides.

Further, in any embodiment, the sequence of a marker gene fragment may be in close proximity to the sequence of an antigen or binding moiety, or fusion protein thereof, encoded by the same nucleic acid. For instance, a marker gene fragment and a promoter element or coding amino acid of a sequence of an antigen or binding moiety, or fusion protein thereof, may be directly adjacent or separated, e.g., by 1 to 200 or more nucleotides, such as 1, 5, 10, 25, 50, 75, 100, 150, or 200 or more nucleotides. In certain embodiments, a marker gene fragment and a promoter element or coding amino acid of a sequence of an antigen or binding moiety, or fusion protein thereof, may be separated, e.g., by 200, 400, 600, 800, or 1,000 nucleotides.

In other embodiments, a functional marker gene requires expression of two separate genes: a first gene encoded by a cellular nucleic acid and a second gene encoded by a viral nucleic acid. Expression of one results, directly or indirectly, in expression of the other, which directly or indirectly results in the manifestation of detectable phenotype. Alternatively, the protein product expressed by the first gene and the second gene may function in concert or in complex to directly or indirectly manifest a detectable phenotype. In such embodiments, the functional marker protein of the present invention may encompass two or more proteins, e.g., a protein complex.

Marker Subunits and Functional Marker Complexes

A binding moiety fusion protein and an antigen fusion protein may each include a subunit of a functional marker complex (antigen marker subunit and binding moiety marker subunit). In some instances, a binding moiety fusion protein includes a first subunit of a functional marker complex, and an antigen fusion protein includes a second subunit of the same functional marker complex. In such embodiments, if the binding moiety and the antigen are a cognate pair and the two fusion proteins are expressed within the same cell, the binding moiety and the antigen may bind within the cell. Binding of a cognate pair will bring together the first and second subunits of the functional marker complex. The functional marker complex may further include one or more additional subunits. One or more additional subunits may be endogenous to the cell in which the fusion proteins are expressed or may be introduced by a vector transferred into the cell.

In particular embodiments, interaction of the first and second subunits of a functional marker complex may depend upon the presence of one or more additional subunits to intermediate cognate pair interaction. In particular, the binding moiety and the antigen may each bind a third subunit. Each of the binding moiety and the antigen may interact with distinct aspects of the third subunit, such that each of the binding moiety and the antigen may simultaneously interact with the third subunit and simultaneous interaction results in formation of a functional marker complex. A third subunit may be a protein, protein complex, peptide, molecule, or polynucleotide (e.g., a single-stranded or double-stranded DNA or RNA molecule). In these particular embodiments, presence of the third subunit is required for formation of a functional marker complex. The third subunit may be endogenous to the cell in which the fusion proteins are expressed or may be introduced by a vector transferred into the cell.

A functional marker complex may manifest a detectable phenotype. In some instances, the functional marker complex performs a function that neither marker subunit or fusion protein is capable of performing in the absence of the other. In other instances, the functional marker complex performs a function that one or both marker subunits or fusion proteins is capable of performing in the absence of the other, but do so with greater frequency or efficiency. The first and second subunits of the marker complex may interact directly, e.g., to function as a single enzyme or factor, or may interact indirectly, e.g., to function in an independent but complementary manner. In some embodiments, the functional marker complex may induce or enhance expression of a particular gene and/or protein. In particular examples, the first and second subunits of a marker complex may include a DNA recognition element (e.g., a DNA-binding domain) and a transcriptional activation element. In such embodiments, the functional marker complex may be adapted to drive expression of a wide variety of endogenous or transgenic genes. Alternatively, the functional marker protein may participate in activities other than the induction of target gene transcription, such as an enzymatic or signaling function. For instance, the functional marker protein may be enzymatically active. Examples of marker subunits are known in the art. For instance, marker subunits have been used in one-hybrid, two-hybrid, and three-hybrid methods, such as bacterial one-hybrid and yeast two-hybrid. As one hybrid, two-hybrid, and three-hybrid methods are, in limited respects, analogous to a subset of the methods presently disclosed, various marking strategies employed therein may be applied to the present invention.

Examples of detectable phenotypes that may result from formation of a functional marker complex include, without limitation, luminescence, fluorescence, antibiotic resistance, toxin resistance, altered growth rate, altered response to an analyte, altered cell structure, altered colony formation, altered auxotrophy, resistance to light (e.g., resistance to UV light), increased thermal resistance, resistance to viral particles, resistance to low pH, resistance to high pH, or salt tolerance. Additional detectable phenotypes (e.g., resistance or tolerance to further biophysical phenomena and/or biochemical reagents), including additional detectable phenotypes that may be linked to the expression of a gene, are known in the art.

For example, a functional marker complex may be, or direct or contribute to the expression of, green fluorescent protein (e.g., gfp), red fluorescent protein (e.g., rfp), yellow fluorescent protein (e.g., yfp), an ampicillin resistance gene (amp), a tetracycline resistance gene (tet), a kanamycin resistance gene (kan), beta galactosidase ($\beta$-gal), an alanine synthesis gene (e.g., argA), a cystein synthesis gene (e.g., cysE), a leucine synthesis gene (e.g., lysA), a threonine synthesis gene (e.g., thrC), and many others known in the art. In particular embodiments, the functional marker complex may manifest a detectable phenotype by directing or contributing to the expression of a gene that manifests the detectable phenotype. In some embodiments, the functional marker complex directs or contributes to the expression of a functional marker gene as described above, e.g., a functional marker gene formed from marker gene fragments upon recombination between two vectors.

Methods for selecting or isolating cells having a detectable phenotype are known in the art. Selecting or isolating one or more cells having a phenotype resulting from expression of a functional marker protein may include, depending upon the detectable phenotype, flow cytometry, culturing a population of cells in the presence of the relevant antibiotic or toxin, culturing a population of cells in the absence of a particular organic compound, or microscopy techniques. Additional methods of selecting and isolating cells having particular detectable phenotypes are known in the art.

Identification of Cognate Pairs by Selective Infection and Recombination

Methods of the present invention may identify one or more cognate binding moieties of one or more antigens. In some instances, a method of the present invention may include a population of cells, each displaying an antigen, and a plurality of attachment-defective virions, each displaying a binding moiety. Each cell may include a nucleic acid encoding the sequence of the antigen displayed on its surface (cellular nucleic acid). The cellular nucleic acid may also include a recombination motif (cellular recombination motif). Each virion may include a nucleic acid encoding the sequence of the binding moiety displayed on its surface (viral nucleic acid). The viral nucleic acid may also include a recombination motif (viral recombination motif). A viral recombination motif may be complementary to a cellular recombination motif.

A population of cells may, for example, be contacted with a plurality of virions, such as a plurality of attachment-defective virions. Incubation of antigen-displaying cells with attachment-defective virions, each virion displaying one or more binding moieties, allows binding of cognate pairs, provided that one or more cognate pairs are present. Binding of cognate pairs rescues the viral attachment defect, selectively permitting infection of one or more cells by one or more virions displaying a cognate binding moiety. Selective infection may include delivery of the viral nucleic acid to the cell. The viral nucleic acid is delivered into the cell in a manner sufficient to allow recombination between the viral nucleic acid and the cellular nucleic acid. Recombination occurs between a recombination motif present on the viral nucleic acid and a complementary recombination motif present on the cellular nucleic acid. One or both of these recombination motifs may be a site-specific recombination motif. In some instances, one or more viral nucleic acids present in a single reaction include one or more recombination motifs or a combination of recombination motifs distinct from that of one or more other viral nucleic acids present in the reaction. In some instances, one or more cellular nucleic acids present in a single reaction include one or more recombination motifs or a combination of recombination motifs distinct from that of one or more other cellular nucleic acids present in the reaction.

In certain embodiments of the present invention, each cell in a population of cells includes a cellular nucleic acid having a particular recombination motif and each virion of a plurality of virions includes a viral nucleic acid having a recombination motif complementary to that of the cells. In certain embodiments of the present invention, each virion of a plurality of virions includes a viral nucleic acid having a particular recombination motif and each cell in a population of cells includes a cellular nucleic acid having a recombination motif complementary to that of the virions. In such embodiments, it is ensured that a viral nucleic acid delivered to a cell by an infecting virion will include a recombination motif complementary to a cellular recombination motif of the infected cell. When a viral nucleic acid delivered to a cell by an infecting virion includes a recombination motif complementary to a cellular recombination motif of the infected cell, a site-specific recombination event occurs.

In some embodiments, a recombination event is facilitated by one or more recombination enzymes. In some instances, the recombination enzyme(s) are encoded by the cell. In other instances, the recombination enzyme(s) are encoded by the virus. A recombination enzyme present in an infected cell may be endogenous to a virus or cell, or may be a transgene, such as a transgene introduced by a vector transferred into the cell. In some instances, one or more cells present in a single reaction include one or more recombination enzymes or a combination of recombination enzymes distinct from that of one or more other cells present in the reaction.

Recombination may result in integration of a viral nucleic acid with a cellular nucleic acid. The integrated product of a viral nucleic acid and a cellular nucleic acid is referred to as a recombinant product. Due to the properties of site-specific recombination events, the particular manner in which the strands of a viral nucleic acid will integrate with the strands of a cellular nucleic acid may be predicted. In some instances, if all or a portion of the sequence of the viral nucleic acid and the cellular nucleic acid is known, the sequence of a recombinant product that would be produced by recombination between a viral nucleic acid and a cellular nucleic acid may be predicted. In some instances, a single particular recombinant product sequence may be predicted. In other instances, the prediction encompasses two or more possible recombinant product sequences.

In particular embodiments, the viral nucleic acid and the cellular nucleic acid each comprise a fragment of a particular marker gene (viral marker gene fragment, cellular marker gene fragment). The two fragments may be portions of a particular functional marker gene such that, if properly arranged by integration, the two fragments have the sequence of a functional marker gene. The two marker gene fragments may be any two portions of a functional marker gene divided such that each fragment is independently incapable of producing a functional marker protein. For instance, the two marker gene fragments may be a promoter and a coding region, respectively.

A viral marker gene fragment and a cellular marker gene fragment may be positioned on a viral nucleic acid and cellular nucleic acid, respectively, such that site specific recombination between the viral nucleic acid and the cellular nucleic acid may be predicted to result in formation of a functional marker gene. The functional marker gene may be capable of expressing a functional marker protein. The functional marker gene may include a promoter such that expression of the functional marker protein may be induced or enhanced by one or more transcription factors present in the cell. In some instances, the functional marker gene is induced or enhanced, directly or indirectly, by one or more stimuli, such as a change in reaction temperature, addition of a metabolite to the reaction, addition of a small molecule to the reaction, or addition of an enzyme to the reaction. Inducible expression systems are known in the art.

In any of the above methods, a binding moiety may, instead of being expressed on a virus, be present on a second cell. For example, the second cell may express the binding moiety on its cell surface. Thus, contacting the second cell with a cell expressing a cognate antigen can result in binding of the two cells. The second cell may include a nucleic acid having, e.g., a recombination motif complementary to the recombination motif of the cell having the antigen. Thus, the second cell can transfer the nucleic acid into the cell having the antigen, such that recombination between the two recombination motifs results in integration of the two nucleic acids. The nucleic acid of the second cell can further include a sequence encoding the binding moiety. Each of the nucleic acids may further include a marker gene fragment, such that integration results in formation of a functional marker gene, e.g., as described above.

Expression of a functional marker gene may result in a detectable phenotype. Examples of detectable phenotypes include, without limitation, luminescence, fluorescence, antibiotic resistance, toxin resistance, altered growth rate, altered response to an analyte, altered cell structure, altered colony formation, or altered auxotrophy. Additional detectable phenotypes that may be linked to the expression of a gene are known in the art.

A method of the present invention may further include detecting, isolating, or selecting one or more cells having a detectable phenotype resulting from expression of a functional marker protein. The method of detection, isolation, or selection may vary with the detectable phenotype. For instance, fluorescent cells may be isolated through flow cytometry. Antibiotic or toxin resistant cells may be isolated through culturing a population of cells in the presence of the relevant antibiotic or toxin. Cells having gained an auxotrophy may be isolated by culturing a population of cells in the absence of the relevant organic compound. Growth phenotypes may be tracked or observed by microscopy, including but not limited to automated microscopy. Additional methods of detecting or isolating cells having particular detectable phenotypes are known in the art. The isolation or selection of cells having a detectable phenotype as described herein may increase the frequency of cells in a population that have the detectable phenotype. The frequency of cells having a detectable phenotype within a selected or isolated population may be, e.g., 10%, 20%, 30%, 40%, 50%, 60%, 70%, 80%, 90%, 95%, 99%, or 100%. Any detectable phenotype of the present invention may manifest in binary, graded, or continuous levels. The nature and distribution of such levels may be dependent upon properties of particular cognate binding pair interactions, such as affinity or avidity.

In other embodiments, the method may be independent of the formation of a functional marker gene. Since infection is required for the formation of a recombinant product including a viral nucleic acid and a cellular nucleic acid, recombinant products of these nucleic acids will only form if a cell displaying an antigen is infected by a virion displaying a cognate binding moiety. As a result, each recombinant product present in a reaction is predicted to encode both members of a particular cognate pair. In some embodiments, recombinant products are isolated from the cells of a reaction and the isolated recombinant products are cloned and/or sequenced to identify cognate pairs.

Recombinant products may be isolated from one or more cells at any point following the contacting of virions with cells. In particular embodiments, polynucleotides are isolated from cells contacted with virions following an incubation period sufficient to allow infection and formation of recombinant products. The isolation of recombinant products may recover all or a portion of one or more recombinant products. In certain instances, recombinant products are isolated by a method of isolating genomic DNA. In certain instances, recombinant products are isolated by a method of isolating plasmid DNA. In certain instances, recombinant products are isolated by a method of isolating RNA.

All or part of one or more recombinant products or amplicons thereof may be cloned and/or sequenced by any means known in the art. Methods of cloning and sequencing are further described herein.

In particular embodiments, all or a portion of one or more recombinant products may be amplified prior to or subsequent to cloning or sequencing. For instance, one or more recombinant products may be amplified using a first oligonucleotide capable of hybridizing to a segment of a recombinant product derived from a viral nucleic acid and a second oligonucleotide capable of hybridizing a segment of a recombinant product derived from a cellular nucleic acid. In this embodiment, the first and second oligonucleotide may flank a segment of the recombinant product that includes a segment originating from a viral nucleic acid and a segment originating from a cellular nucleic acid (hybrid segment). The hybrid segment may include all or a portion of the sequence of an antigen, all or a portion of the sequence of a binding moiety, or both. In some instances, each viral nucleic acid may include one or more universal priming sequences and each cellular nucleic acid may include one or more universal priming sequences. In such embodiments, a pair of oligonucleotides including an oligonucleotide capable of hybridizing to a viral universal priming sequence and an oligonucleotide capable of hybridizing to a cellular universal priming sequence may be used to amplify a hybrid segment. In other embodiments, an antigen sequence may be flanked by two cellular universal priming sequences, a binding moiety sequence may be flanked by two viral priming sequences, or both, such that one or more antigen sequences, one or more binding moiety sequences, or both may be independently amplified. In any of the present embodiments, such as those encompassing amplification or sequencing, one or more recombinant products or one or more amplicons thereof may include one or more variable priming sequences, as further described herein. Since variable priming sequences include one or more variable nucleotide positions, they may be used to selectively amplify all or a portion of one or more particular recombinant products or amplicons thereof.

Identification of Cognate Pairs by Co-Expression and Recombination

In some methods of the present invention, a cognate binding moiety of one or more antigens is identified by co-expression of a binding moiety fusion protein and an antigen fusion protein within a single cell. In such embodiments of the present invention, cells, antigens, binding moieties, recombination motifs, recombination enzymes, marker gene fragments, functional maker genes, and related subject matter are consistent with the descriptions above.

In some embodiments, co-expression of at least a binding moiety fusion protein and an antigen fusion protein is achieved by transfection of a single cell with at least two vectors: a vector encoding a binding moiety fusion protein (binding moiety vector) and a vector encoding an antigen fusion protein (antigen vector). Either or both of the vectors may additionally include a recombination motif. In certain embodiments, the recombination motif is a site-specific recombination motif. For instance, a binding moiety vector may include a particular site-specific recombination motif and an antigen vector may include a site-specific recombination motif complementary to that of the binding moiety vector. In some instances, one or more binding moiety vectors present in a single reaction includes one or more recombination motifs or a combination of recombination motifs distinct from that of one or more other binding moiety vectors present in the reaction. In some instances, one or more antigen vectors present in a single reaction include one or more recombination motifs or a combination of recombination motifs distinct from that of one or more other antigen vectors present in the reaction. The vector may be a circular DNA molecule such as a plasmid. The vector may be a viral vector, cosmid, artificial chromosome, or transposon. At least one binding moiety vector and one antigen vector may be transferred into a single cell in order to sample a candidate cognate pair. In some embodiments, one or more distinct binding moiety vectors and one or more distinct antigen vectors are transferred into a plurality of cells in order to sample a plurality of candidate cognate pairs.

Transfer of one or more vectors into a cell may occur through transformation, transduction, transfection, mating, chemical fusion, or any other means known in the art. Any of one or more vectors may be transferred into a cell by a virus or from another cell. For instance, the cell may be a bacterial cell and either or both vectors may be transferred into the cell by phage. In particular embodiments, one or more vectors are transfected into a cell in a manner mediated by interaction of a molecule displayed by the cell and a molecule displayed by the entity transferring the vector into the cell. Laboratory methods of transfection and transduction are known in the art, as are other methods of transferring a polynucleotide into a cell.

A gene encoding an antigen fusion protein and/or a gene encoding a binding moiety fusion protein may be capable of expression in a cell into which they are transfected. Expression of one or more antigen fusion protein genes or one or more biding moiety fusion protein genes may be driven by a promoter such that expression of one or more of these genes occurs within the cell into which the gene was transferred. A binding moiety fusion protein and an antigen fusion protein may be expressed from distinct promoters. Alternatively, a promoter from which a binding moiety fusion protein is expressed may be the same as a promoter from which an antigen fusion protein is expressed. Expression of one or more genes transferred into a cell may be driven, e.g., by one or more proteins expressed by the infected cell. In such embodiments, one or more of the proteins mediating expression may be endogenous to the cell. In some embodiments, one or more proteins may have been introduced to the cell by a vector transferred into the cell.

In some instances, expression of a gene transferred into a cell are induced or enhanced, directly or indirectly, by one or more stimuli, such as a change in reaction temperature, addition of a metabolite to the reaction, addition of a small molecule to the reaction, or addition of an enzyme to the reaction. Inducible expression systems are known in the art.

In some instances, expression are modulated by codon optimization or other cell-type specific mechanisms. Methods of expressing proteins in various cell types of the present invention are known in the art.

In some methods of the present invention, a recombination event between a binding moiety vector and an antigen vector occurs. In such embodiments, recombination is mediated by one or more recombination motifs. For example, in certain embodiments of the present invention, each binding moiety vector includes a particular recombination motif and each antigen vector includes a recombination motif complementary that of the binding moiety vectors. In some embodiments of the present invention, each antigen vector includes a particular recombination motif and each binding moiety vector includes a recombination motif complementary to that of the antigen vectors. In such embodiments, it is ensured that an antigen vector and a binding moiety vector transfected into a cell include complementary recombination motifs. When a biding moiety vector and an antigen vector transfected into a single cell include complementary site-specific recombination motifs, a site-specific recombination event may occur. The resultant recombinant product will include an antigen sequence and a binding moiety sequence having been transfected into the same cell.

In some embodiments, a recombination event between an antigen vector and a binding moiety vector is facilitated by one or more recombination enzymes. In some instances, one or more recombination enzymes are encoded by a cell. A recombination enzyme present in an infected cell may be endogenous to a cell, or may be a transgene, such as a transgene introduced by a vector transferred into the cell. In some instances, one or more recombination enzymes are encoded by a binding moiety vector, an antigen vector, or both. In some instances, one or more cells present in a single reaction include one or more recombination enzymes or combination of recombination enzymes distinct from that of one or more other cells present in the reaction.

In some embodiments, a recombination event occurs in a cell infected by a virion. In alternate embodiments, the recombination event does not occur in the virion-infected cell, but rather, two nucleic acids containing complementary recombination motifs (e.g., one originating from the virion and one originating from the cell) are packaged into a new virion particle produced by the infected cell, such that when the new virion particle is released and subsequently infects a further cell, recombination occurs between the two nucleic acids in the infected further cell.

In various embodiments of the present invention, recombination between an antigen vector and a binding moiety vector does not depend upon cognate pair interaction. In these instances, cells expressing a detectable phenotype indicative of cognate pair interaction may be isolated or selected.

A method of the present invention may include detecting, isolating, or selecting one or more cells having a phenotype resulting from expression of a functional marker complex. The method of detection, isolation, or selection may vary with the detectable phenotype. For instance, fluorescent cells may be isolated through flow cytometry. In particular embodiments, cells are incubated under conditions adverse to the survival of cells in which formation of a functional marker complex did not occur. For instance, in some embodiments, a functional marker complex manifests an antibiotic resistance phenotype, such that cells lacking a functional marker complex are more susceptible to a particular antibiotic than those that include one or more functional marker complexes. Antibiotic or toxin resistant cells may be isolated through culturing a population of cells in the presence of the relevant antibiotic or toxin. Cells having gained an auxotrophy may be isolated by culturing a population of cells in the absence of the relevant organic compound. Growth phenotypes may be tracked or observed by microscopy. Additional methods of detecting and isolating cells having particular detectable phenotypes are known in the art. Any detectable phenotype of the present invention may manifest in binary, graded, or continuous levels. The nature and distribution of such levels may be dependent upon properties of particular cognate binding pair interactions, such as affinity or avidity.

Recombinant products may be isolated from one or more cells at any point following substantial isolation or selection of cells including one or more functional marker complexes. In particular embodiments, polynucleotides are isolated from cells following incubation in a manner sufficient to allow functional marker complex formation. The isolation of recombinant products may recover all or a portion of one or more recombinant products. In certain instances, recombinant products are isolated by a method of isolating genomic DNA. In certain instances, recombinant products are isolated by a method of isolating vector DNA.

In particular embodiments, the functional marker complex may function as, or direct or contribute to expression of, a recombination enzyme, such that recombination only, selectively, or preferentially occurs in cells into which a vector encoding an antigen and a vector encoding a cognate binding moiety have been transferred. In certain embodiments, an antigen vector and a binding moiety vector include complementary site-specific recombination motifs and further include a first and second marker gene fragment, respectively, such that site-specific recombination results in formation of a functional marker gene. Expression of the functional marker gene complex may manifest a detectable phenotype. The detectable phenotype may be used to isolate or select cells expressing a functional marker complex.

In certain embodiments in which the functional marker complex is a recombination enzyme that facilitates recombination between an antigen vector and a binding moiety vector, cognate pairs are identified without the use of a detectable phenotype. Instead, recombinant products may be isolated from a population of cells following incubation in a manner sufficient to allow recombinant product formation. The isolation of recombinant products may recover all or a portion of one or more recombinant products. In certain instances, the recombinant product may be isolated by a method of isolating genomic DNA. In certain instances, recombinant product may be isolated by a method of isolating vector DNA.

In particular embodiments, a portion of one or more recombinant products is amplified. For instance, one or more recombinant products may be amplified using a first oligonucleotide capable of hybridizing to a segment of a recombinant product having originated from an antigen vector and a second oligonucleotide capable of hybridizing a segment of a recombinant product having originated from a binding moiety vector. In this embodiment, the first and second oligonucleotide may flank a segment of the recombinant product that includes both a segment originating from an antigen vector and a segment originating from a binding moiety vector (hybrid segment). The hybrid segment may include all or a portion of the sequence of an antigen, all or a portion of the sequence of a binding moiety, or both. In some instances, each antigen vector may include one or more universal priming sequences and each binding moiety vector may include one or more universal priming sequences such that amplification using oligonucleotides to a viral universal priming sequence and a cellular universal priming sequence may amplify a hybrid segment. In other embodiments, an antigen sequence may be flanked by two cellular universal priming sequences, a binding moiety sequence may be flanked by two viral priming sequences, or both, such that one or more antigen sequences, one or more binding moiety sequences, or both may be amplified. In any of the above embodiments, such as those encompassing amplification or sequencing, one or more recombinant products or one or more amplicons thereof may include one or more variable priming sequences. Since variable priming sequences include one or more variable nucleotide positions, they may be used to selectively amplify all or a portion of one or more particular recombinant products or amplicons thereof.

Cloning or Sequencing

In any of the above methods, a cognate pair of the present invention may be identified by cloning or sequencing all or a portion of one or more recombinant products. In certain embodiments, a cognate pair of the present invention may be identified by determining a wobble barcode of one or more recombinant products (e.g., by sequencing or by SNP genotyping). Methods of cloning and sequencing are well known in the art, including methods of deep sequencing and NextGeneration sequencing. Sequencing may include next generation sequencing technologies, such as Hyseq2500, Ion Torrent sequencing, Illumina sequencing, 454 sequencing, SOLiD sequencing, or nanopore sequencing. Additional methods of sequencing are known in the art. An antigen sequence and a binding moiety sequence present in the same recombinant product may encode a cognate pair.

In some instances, the total number of consecutive nucleotides that must be sequenced in order to completely define the sequences of an antigen and cognate binding moiety encoded by a particular recombinant product is greater than the average read length of a given method of sequencing. When the read length of a method of sequencing is shorter than the total length of a sequence to be identified, multiple, overlapping reads are assembled based on overlap homology. Cumulatively, assembly of overlapping reads may produce a sequence greater in length than any of the component reads. Read assembly becomes ineffective when a nucleic acid material being sequenced includes two or more segments of a length similar to or greater than the read length that cannot be distinguished. This limitation is relevant when sequencing a plurality of recombinant products that encode two or more antigens having significant sequence similarity or two or more binding moieties having significant sequence similarity.

To overcome the challenge of sequencing two or more similar sequences, the sequences of one or more polynucleotides encoding a binding moiety or antigen of the present invention may be engineered to introduce nucleotide variability. In particular instances, the introduction of variability does not alter the protein encoded by the polynucleotide. This result may be achieved by increasing the variability of antigen or binding moiety sequences by modifying non-coding positions and/or wobble positions. A wobble position is a position of a codon that may be filled by any one of two, three, or four nucleobases selected from adenine, guanine, cytosine, and thymine (uracil in mRNA) without altering the amino acid encoded by the codon. Thus, the particular substitutions that may be made within a codon may depend upon the amino acid that the codon encodes and the set of other codons that also encode the same amino acid. The particular substitutions that may be made within a codon may depend upon the organism in which the codon is to be translated, since organisms may vary in codon usage. Accordingly, the particular conservative wobble position substitutions that may be made in a given codon in a given organism may be ascertained from the art. The present invention therefore utilizes the recognized degeneracy of the genetic code to increase sequence variability and improve sequencing outcomes. Any introduction of variation may result in the formation of a variable priming sequence.

Variable Priming Sequences

In any of the above embodiments, such as those encompassing amplification, cloning, or sequencing, all or a portion of one or more recombinant products or all or a portion of one or more amplicons thereof may include one or more variable priming sequences. A variable priming sequence is a segment of a polynucleotide that may serve as a hybridization site for an oligonucleotide and that includes one or more variable nucleotide positions. Since variable priming sequences include one or more variable nucleotide positions, they may be used to selectively amplify all or a portion of one or more particular recombinant products or amplicons thereof. A variable priming sequence may include only variable nucleotide positions or may include a combination of variable and constant nucleotide positions. For instance, a variable priming sequence may include 1-50 variable nucleotide positions, such as 1, 2, 3, 4, 5, 10, 20, 30, 40, or 50 variable nucleotide positions. In any of these embodiments, the remaining positions in the variable priming sequence may be constant. A variable priming sequence may also be longer than 50 nucleotides. Insofar as the number of nucleotide positions included in the priming sequence is not strictly limited, any given length of variable priming sequence may include from 0.1% to 100% variable nucleotide positions, such as 0.1%, 1%, 2%, 3%, 4%, 5%, 10%, 20%, 30%, 40%, 50%, 60%, 70%, 80%, 90%, or 100% variable nucleotide positions. In any arrangement having both constant and variable nucleotide positions, the constant or variable positions may be respectively contiguous or non-contiguous. If non-contiguous, the constant or variable positions, respectively, may be regularly or irregularly dispersed throughout the variable priming sequence.

The variable priming sequences may be synthesized such that a given variable position may be filled by one of any two, three, four, or five of adenine, guanine, cytosine, thymine, and uracil. In other embodiments, the variable positions may also or alternatively be filled by one or more artificial, synthesized, modified or unnatural nucleotides, or any nucleotide other than unmodified adenine, guanine, cytosine, thymine, or uracil. In some instances, an artificial nucleotide may pair with an unmodified, natural nucleotide. In others, an artificial nucleotide may selectively pair with another artificial nucleobase to form an artificial base pair. An exemplary artificial base pair may be a 3-fluorobenzene self-pair, a dSICS and dMMO2 pair, a d5SICS and dMMO2 pair, or a d5SICS and dNaM pair. The variable priming sequences may be synthesized to include any combination of adenine, guanine, cytosine, thymine, uracil, and alternative or synthetic nucleobases. The identity of the nucleotide options selected to fill any one variable position of a variable priming sequence may not bear upon the nucleotide options that may be selected to fill any other variable position within the same variable priming sequence or otherwise. Any subset of available natural, unnatural, modified, synthetic or artificial nucleotides may be provided independently to fill any particular position.

The nucleotides selected to fill a particular variable position may be provided in equal molar proportions. Alternatively, one or more of the selected nucleotides may be provided in excess to one or more other selected nucleotides. In some embodiments, a variable priming sequence is synthesized to incorporate a nucleotide from the available or selected nucleotide possibilities in an essentially randomized manner. In others, incorporation of one or more of the selected nucleotides is favored over the incorporation of one or more other selected nucleotides.

Upon synthesis of a nucleic acid molecule having a variable priming sequence, the sequence of the variable priming sequence become determined. Insofar as related variable priming sequences may vary at the variable positions, any particular determined arrangement of nucleotides for a variable priming sequence may be referred to as a permutation. The number of distinct permutations may be a function of the number of variable positions and the number of possible nucleotides by which each variable position may be filled.

Multiplexing

Any of the above methods may be applied to a single cell, a single antigen, or a single binding moiety. Alternatively, any of the above methods may be applied to a population of cells, a plurality of distinct antigens, and a plurality of distinct binding moieties.

In some embodiments, the average number of distinct transgenic antigens displayed by any given cell of a population of cells is less than or equal to 0.1, 0.2, 0.3, 0.4, 0.5, 0.6, 0.7, 0.8, 0.9, 1, 2, or 3. In some embodiments, the average number of distinct transgenic binding moieties displayed by any given virion of a population of virions is less than or equal to 0.1, 0.2, 0.3, 0.4, 0.5, 0.6, 0.7, 0.8, 0.9, 1, 2, or 3. In some embodiments, the average number of distinct antigen vectors received by any given cell of a population of cells is less than or equal to 0.1, 0.2, 0.3, 0.4, 0.5, 0.6, 0.7, 0.8, 0.9, 1, 2, or 3. In some embodiments, the average number of distinct binding moiety vectors received by any given cell of a population of cells is less than or equal to 0.1, 0.2, 0.3, 0.4, 0.5, 0.6, 0.7, 0.8, 0.9, 1, 2, or 3.

An embodiment of the present invention may include a population of 1 to $10^{12}$ cells, such as $10^2$, $10^4$, $10^6$, $10^8$, $10^{10}$, or $10^{12}$ or more cells. An embodiment of the present invention may include 1 to $10^{12}$ distinct transgenic antigens, such as $10^2$, $10^4$, $10^6$, $10^8$, $10^{10}$, or $10^{12}$ or more distinct transgenic antigens. One or more, or all, of these antigens may be present in a cell, present in a vector, present in a fusion protein, or otherwise utilized in any manner described herein. An embodiment of the present invention may include 1 to $10^{12}$ distinct transgenic binding moieties, such as $10^2$, $10^4$, $10^6$, $10^8$, $10^{10}$, or $10^{12}$ or more distinct transgenic binding moieties. One or more, or all, of these binding moieties may be present in a virion, present in a vector, present in a fusion protein, or otherwise utilized in any manner described herein.

In particular embodiments, binding moieties of the present invention include a pool of binding moieties isolated or derived from a particular cell population. For instance, a pool of binding moieties may include binding moieties isolated or derived from a population of cells isolated from one or more inoculated subjects. In other instances, the binding moieties of the present invention may be a pool of binding moieties isolated or derived from a population of cells isolated from one or more subjects that are naïve to a particular inoculant. A population of cells isolated from one or more subjects may be a population of B-cells and the binding moieties may be antibodies. A population of binding moieties may further be isolated or derived from a population including two or more distinct subpopulations.

In particular embodiments, antigens of the present invention include a pool of antigens isolated or derived from a particular population of viruses or cells. For instances, a pool of antigens may include antigens isolated or derived from virions or cells of one or more of a pathogenic virus, a pathogenic prokaryote, a pathogenic eukaryote, a pathogenic cell type (e.g., a human pathogenic cell type such as a particular cancer cell type), or an infected cell type (e.g., human cells infected with a particular pathogenic virus or bacterium).

In some embodiments of the present invention, a pool of binding moieties and a pool of antigens will be present in a single reaction. In particular embodiments, one or more or all possible pairings of a binding moiety and an antigen present in a reaction may be sampled.

In certain embodiments, one or more binding moieties or one or more antigens of the present invention are derived from a synthesized polynucleotide, e.g., a polynucleotide synthesized by a method of parallel polynucleotide synthesis. Methods of polynucleotide synthesis include large scale parallel methods by which a plurality of diverse nucleotide sequences may be synthesized. Polynucleotides produced by a templated method of polynucleotide synthesis may include greater variability than the template sequences. Variability may be introduced, e.g., by polymerase error (e.g., one or more sequence changes introduced by a standard polymerase or error-prone polymerase), chemical synthesis error, or chemical mutagenesis. Other methods of introducing variation are known in the art. Any method for the synthesis of polynucleotides may be suitable to the present invention. A pool of binding moieties or a pool of antigens of the present invention may include a plurality of proteins or peptides derived from a population of polynucleotide variants of a single polynucleotide sequence or a population of polynucleotide variants of multiple polynucleotide sequences. A pool of binding moieties or a pool of antigens of the present invention may include a plurality of proteins or peptides derived from a population of polynucleotides synthesized by a method of large scale parallel polynucleotide synthesis. A method of polynucleotide synthesis may include synthesis on a chip, synthesis by emulsion, synthesis from constituent oligonucleotides, or synthesis by any other means known in the art.

The capacity of the present invention to identify cognate pairs from amongst a plurality of antigens and a plurality of binding moieties within a single reaction is amongst the advantageous features of the present invention.

Library Generation

Figure 2:
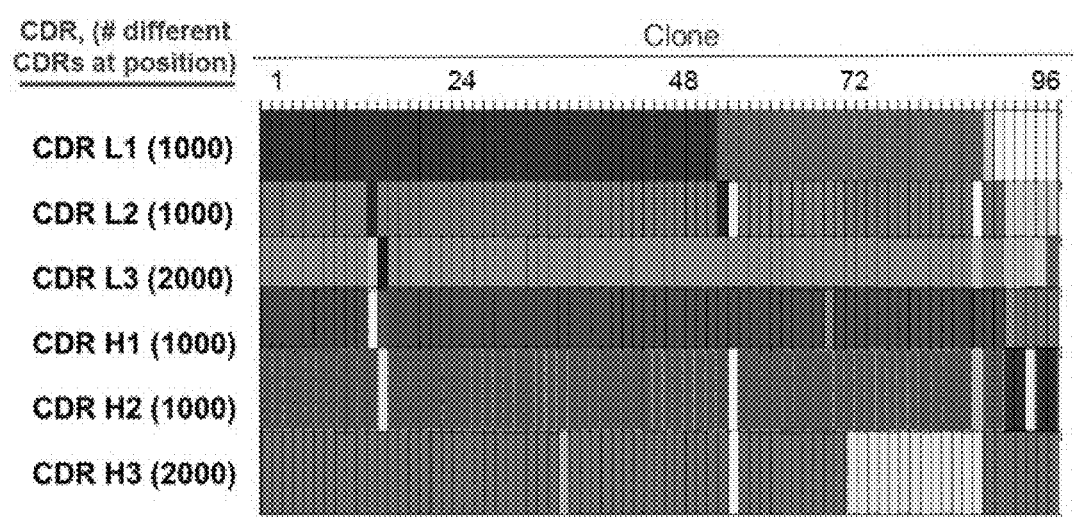
FIG. 2 is a schematic showing a pre-defined CDR library with enrichment of specific CDR nucleic acid sequences. The same color within a CDR position (L1, L2, L3, H1, H2, or H3) indicates the same pre-defined CDR and between different CDRs indicates different nucleic acid sequences. Specific CDR sequences were enriched during selection.

In some embodiments, the method of the present invention may be used to generate nucleic acid variants encoding a plurality of antibodies or fragments thereof (e.g., a plurality of CDRs). The method of the present invention may yield a library of nucleic acid variants with a total number of variants greater than about 1E+05, such as about 1E+05, 1E+06, 1E+07, 1E+08, 1E+09, 1E+10, 1E+11, or 1E+12 variants or more. A library of nucleic acid sequences encoding CDRs may be synthesized on a chip (FIGS. 1-2), by emulsion, from constituent oligonucleotides, or by any other means of synthesis known in the art. The nucleic acid sequence variants of interest may be isolated and combined with sequences that are substantially identical (e.g., at least 75%, 80%, 85%, 90%, 95%, 96%, 97%, 98%, 99%, or 100% sequence identity) to the isolated nucleic acid sequences of interest or a fragment thereof. The sequences of substantial identity may be single stranded DNA (ssDNA) molecules, e.g., circular ssDNA intermediaries, and the isolated nucleic acids of interest may be ligated into the ssDNA intermediaries to form double stranded DNA molecules, e.g., heteroduplex DNA.

Ligation may be achieved by co-incubation of the isolated nucleic acids and ssDNA intermediaries under conditions of denaturation (e.g., at a denaturing temperature), followed by conditions that allow annealing of the isolated nucleic acids and ssDNA intermediaries (e.g., a gradual cooling in temperature). The denaturing temperature may be about 90° C., e.g., about 80° C., 82° C., 84° C., 86° C., 88° C., 92° C., 94° C., 96° C., or 100° C. The annealing temperature may be about 55° C., e.g., about 50° C., 51° C., 52° C., 53° C., 54° C., 56° C., 57° C., 58° C., or 60° C. The gradual cooling may occur at a rate of about −1° C. per minute, e.g., about −0.5° C., −1.5° C., −2° C., −2.5° C., or 3° C. The heteroduplex DNA may then be transformed into cells, such as E. coli cells, thereby generating a library of variants of interest.

In other embodiments, the method of the present invention may be used to generate a nucleic acid sequence encoding an antibody by providing a mixture of nucleic acids encoding a library of CDRs and a set of oligonucleotide primers targeting particular regions of the nucleic acids. The nucleic acids encoding the desired CDRs may then be isolated by amplification with the oligonucleotide primers. A support (e.g., a bead) including one or more capture oligonucleotides may also be provided. A segment of each isolated nucleic acid may be complementary to at least one capture oligonucleotide (e.g., a support-bound nucleic acid molecule having at least one segment of one strand that is capable of hybridizing to an identifying sequence of a nucleic acid of interest).

Next, a contacting step may result in hybridization of the isolated nucleic acids and the capture oligonucleotides to form a capture complex (e.g., a complex that is formed when a support having one or more capture oligonucleotides is contacted with one or more corresponding isolated nucleic acids of interest). Accordingly, the occupancy of capture oligonucleotides present on a capture complex may be 100%, less than 100%, less than 90%, less than 80%, less than 70%, less than 60%, less than 50%, less than 25%, less than 20%, less than 15%, less than 10%, less than 5%, or less than 1%. The capture complex may be emulsified in an emulsion medium (e.g., a water-in-oil emulsion), optionally with reaction reagents (e.g., a strand-displacing polymerase) sufficient for an adjoining extension reaction to occur, such that the emulsion medium forms an emulsion droplet including the capture complex and reaction reagents. The emulsion is then incubated at a temperature regimen sufficient for an adjoining extension reaction to occur, such that a polynucleotide may be formed from the two or more isolated nucleic acids. Temperature regimens appropriate to numerous adjoining extension reactions are known in the art. In any of the above embodiments, each recombinant product may be capable of expressing an antibody or fragment thereof, e.g., a single-chain variable fragment antibody, a functional immunoglobulin heavy chain and a functional immunoglobulin light chain that are capable of interacting to form a single functional binding moiety, or an IgG binding moiety.

A method of the present invention may further include generating a library of variants of a sequence of interest by the following steps: a. contacting cells with DNA (e.g., a vector) including the sequence of interest in excess of the cells, and b. transforming the vector into the cells. Such methods may allow for the generation of a library of variants including the sequence of interest with a high concentration of transformed recombinant vectors, e.g., a high transformation efficiency. Transformation of cells with DNA may be accomplished by any method known in the art. Examples include electroporation, chemical transformation, and heat shock transformation. Cells may be treated to optimize competence for the selected method of transformation. In some embodiments, DNA may be purified prior to transformation. The DNA, e.g., vector, may be supplied in excess of the cells at about 10%, 20%, 30%, 40%, 50%, 60%, 70%, 80%, 90%, 100%, or more.

The transformants are a library of variants of the sequence of interest. Transformants may be cultured in a recovery media. Individual aliquots may be combined in recovery media or cultured separately. After recovery, the cultured transformants may be pelleted. Pelleted transformants may be stored at a temperature of −20° C. or less. Alternatively, pelleted transformants may be resuspended. The resuspended library may be incubated with a helper phage, resulting in a phage display library. Alternatively some or all aliquots of the resuspended library may be stored at a temperature of −20° C. or less. The phage display library may be pelleted. The pelleted phage display library may be stored at a temperature of −20° C. or less. Alternatively, the pelleted phage display library may be resuspended. The resuspended pelleted phage display library may be stored at a temperature of −20° C. or less. A cultured library of variants, resuspended library of variants, phage display library, or resuspended phage display library may be optionally diluted and plated onto culture plates.

Transformation of cells with saturating amounts of DNA may result in a larger library of recombinants than under non-saturating conditions. The capacity of the present invention to create libraries with greater transformation efficiency is another advantageous feature of the present invention.

Barcodes

A barcode of the present invention is a nucleic acid identifier that can be distinguished from other barcodes by its nucleic acid sequence. A barcode can be attached to or be contained within a molecule, thereby "tagging" the molecule. For example, a barcode can be attached to another nucleic acid, e.g., a nucleic acid encoding a CDR or antibody, a nucleic acid component of a cognate pair of the invention, or a cognate pair of the invention. A barcode can include, e.g., a continuous and/or discontinuous series of nucleotides. In some embodiments, a barcode can include a codon encoding an amino acid and/or nucleotides that do not encode an amino acid. A barcode can be a contiguous segment of nucleotides attached to a molecule of interest (e.g., 1, 2, 3, 4, or more nucleotides). Alternatively, a barcode can be a wobble base barcode, such as described herein. In some instances, a barcode can include both a wobble base barcode and a non-wobble base barcode (e.g., a contiguous segment of nucleotide acids tagging a molecule of interest). In certain embodiments, a molecule of interest can be tagged with a plurality of barcodes (e.g., at least one contiguous barcode and at least one wobble barcode, a plurality of contiguous barcodes, and/or a plurality of wobble barcodes). The sequence of a barcode can be randomly assigned or pre-determined (e.g., a sequence complementary to an identifying sequence on a tile oligonucleotide to be captured). A barcode of the invention can have a length of about, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt), or more. For example, barcodes can have lengths ranging between about 1-4 nucleotides, 1-10 nucleotides, 1-20 nucleotides, 1-50 nucleotides, 1-100 nucleotides, 1-200 nucleotides, or 100-200 nucleotides. In some embodiments, a barcode can be constructed in combinatorial fashion by combining randomly selected oligonucleotide indexes (e.g., about 1, 2, 3, 4, 5, 6, 7, 8, 9, or 10 indexes).

Wobble Base Barcodes

A barcode used to identify a molecule of interest (e.g., a nucleic acid of interest, such as a nucleic acid encoding a CDR or antibody, a nucleic acid component of a cognate pair of the invention, or a cognate pair of the invention) may be a wobble base barcode. As well known in the art, a nucleic acid encoding an amino acid sequence (e.g., an amino acid sequence for a polypeptide or protein) includes sets of three-nucleotide codons, each of which encodes a single amino acid in the sequence. A particular amino acid can be encoded by more than one possible codon. For example, leucine can be encoded by six distinct codons (TTA, TTG, CTT, CTC, CTA, or CTG). Thus, it is possible to mutate a polypeptide-encoding nucleic acid sequence in a translationally silent manner, by altering nucleotides within a codon that do not affect the amino acid encoded by the codon. For example, the third nucleotide in a CTT codon can be mutated from a T to an A, C, or G without changing the amino acid (leucine) encoded by the codon. This CTT codon can also be mutated at two distinct positions, for example, changing the first nucleotide to a T and the third nucleotide to either an A or a G, to yield either TTA or TTG, both of which also encode leucine. Such nucleotide positions that can be changed without affecting the resultant amino acid encoded by the codon are referred to as "wobble positions" or "wobble bases."

Figure 3:
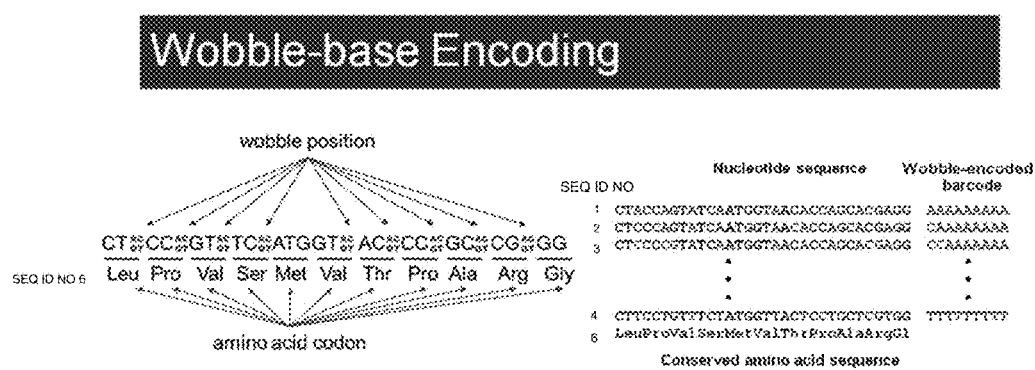
FIG. 3 is a schematic showing the encoding of a barcode sequence into the wobble positions of a nucleotide sequence that encodes an amino acid sequence.

The present invention features barcodes made up only of the nucleotides occupying wobble positions of a polypeptide-encoding nucleic acid. In other words, translationally-silent changes to wobble base(s) in a codon can be used as a means for inserting an identifier into the coding sequence of the nucleic acid without changing the amino acid sequence translated from the nucleic acid, and without requiring the attachment of a nucleic acid barcode sequence external to the coding sequence. A gene sequence can thus be barcoded, for example, without adding an external barcode or changing the sequence of the encoded protein. An example of wobble positions in a polypeptide-encoding nucleic acid sequence is shown in FIG. 3. In this example, the third nucleotide of each codon is a wobble position that can be any one of A, C, G, or T, without altering the polypeptide encoded by the nucleic acid. Thus, these wobble positions can encode information (e.g., an identifier sequence) unique to this particular nucleic acid (or copies thereof), which can be read, e.g., by sequencing the nucleic acid or using single nucleotide polymorphism (SNP) genotyping methods well known in the art. For example, inserting an A into each wobble position can yield a wobble base barcode that reads "AAAAAAAAA." Alternate instances of the nucleic acid can each receive variations on this wobble base barcode (e.g., "CAAAAAAAA," "CCAAAAAAA," or "TTTTTTTTT").

The length of a wobble base barcode can vary depending on the number of identifiers required for a particular application. For example, a small set of up to six variants can be identifiably labeled at a single identifier codon encoding serine or leucine, each of which is encoded by six distinct codons. Individual wobble base barcodes can contain, for example, 1 or more wobble bases (e.g., about 1, 2, 3, 4, 5, 6, 7, 8, 9, 10, 11, 12, 13, 14, 15, 16, 17, 18, 19, 20, or more wobble bases). Preferably, wobble base barcodes include between 1-4 nucleotides, 1-10 nucleotides, 1-20 nucleotides, 1-50 nucleotides, 1-100 nucleotides, 1-200 nucleotides, or 100-200 nucleotides. The wobble bases can be located, e.g., in consecutive codons or in nonconsecutive codons. Thus, a wobble base barcode can span a greater number of codons than the number of nucleotides in the barcode. For example, any two identifier codons of a particular wobble base barcode can span at least about 0, 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, 1000, 1500, 2000, or more codons of the nucleic acid variant identified by the wobble base barcode. Preferably, two identifier codons of a particular wobble base barcode can span at least about 0-4 codons (e.g., about 1, 2, 3, 4, 5, 6, 7, 8, 9, 10, 20, 50, 100, 200, 500, 1000, 1500, 2000, 3000, 4000, 5000, 6000, 7000, 8000, 9000, 10,000, or more nucleotides). In some embodiments, wobble base barcodes are located on different strands of a nucleic acid. For example, some wobble bases in a barcode can be located on the Watson strand, while others can be located on the Crick strand. In certain embodiments, a nucleic acid variant can include at least two wobble base barcodes, one located on the Watson strand and one located on the Crick strand. In one embodiment, one of the wobble base barcodes is positioned at the 5' end of the coding sequence (for example, within 0-30 nucleotides of the 5' end, e.g., within about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides) and one of the wobble base barcodes is positioned at the 3' end of the coding sequence (for example, within 0-30 nucleotides of the 3' end, e.g., within about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides). In some instances, a wobble base barcode can include nucleotides present on distinct nucleic acid fragments in the same particle (e.g., virion or cell). Such distinct fragments can be, e.g., integrated to produce a single nucleic acid containing the wobble base barcode.

The codons selected as identifier codons can be, for example, a set of codons located in close proximity to each other (e.g., close enough to be sequenced in a single next generation sequencing read). In some embodiments, the codons selected as the identifier codons in a set of nucleic acid variants include every instance of codons encoding one or more particular amino acids (e.g., leucine and/or serine) in the sequences of the nucleic acid variants. For example, a pool of nucleic acid variants can be labeled with wobble base barcodes including each of the serines and/or leucines in the nucleic acid variants. If there are, for example, ten serines and/or leucines in each of the nucleic acid variants, a total of up to $6^{10}$ distinct serine/leucine wobble base barcodes can be constructed, as each of the serines and/or leucines can be encoded by one of six distinct codons.

The wobble barcodes identifying particular nucleic acid variants in a pool of such variants will generally encode polypeptides sharing high amino acid sequence identity (e.g., at least 70%, 80%, 85%, 90%, 95%, 97%, 98%, 99%, or 100% amino acid sequence identity; preferably 100% amino acid sequence identity). As such, the wobble barcodes can encode constant portions of the polypeptide. The polypeptide may further include one or more variable portions, in which the amino acid sequences encoded by the nucleic acid variants can also vary. For example, the polypeptides can include variable CDR sequences while the wobble barcodes are restricted to low-variation domains, constant domains, and/or framework regions.

In some embodiments, a nucleic acid sequence can include wobble base barcodes useful for both identifying and amplifying the sequence. For example, PCR primers can be designed that are complementary to flanking wobble barcode sequences. In certain embodiments, the nucleic acid sequence can include wobble base barcodes on both the 5' and 3' ends. Identification of this nucleic acid sequence can be performed by determining one or both of the wobble base barcode sequences. For example, an 18 base sequence on the 5' end can be sequenced, which includes six codons, each with, e.g., a single wobble position (FIG. 4). Thus, this sequencing results in the determination of a 6-nucleotide wobble base barcode, which can be used to identify the nucleic acid. Wobble base barcodes including six wobble positions can, for example, be used to identify up to 4096 variants. Additional sequence complexity rises as a factor of 4, such that, e.g., 8 wobble bases could be used to identifiably label up to 65,000 variants. The nucleic acid can further include framework sequences held constant, for example, between variants of the nucleic acid. As such, primers can be designed that target the constant framework sequences. Primers can also include at least a portion of the wobble barcodes, thereby permitting allele-specific amplification based on the unique wobble barcodes. Any specific variant can be amplified from a mixture containing a plurality of variants (e.g., all variants in a pool) using a set of orthologous primers and allele-specific PCR. For example, a specific variant can be amplified from a pool of up to 4096 variants, each having a 5' and 3' wobble barcode, using a limited set of 128 orthologous primers and allele-specific PCR. In one embodiment, each nucleic acid variant includes flanking framework regions, a 5' wobble barcode, a 3' wobble barcode, and a central variable sequence encoding, for example, a CDR (FIG. 4).

Check-Sums

A wobble base barcode can further incorporate a check-sum at one or more codons to increase accuracy of barcode decoding. A check-sum can be, e.g., a small-size datum from a block of digital data (e.g., a block of data containing nucleic acid sequence information) useful for detecting errors that may have been introduced during its transmission, encoding, decoding, reading, or storage. The check-sum value can include, for example, particular nucleotides indicating proper encoding of earlier wobble bases in the wobble base barcode. For example, the last of 10 identifier codons can be a check-sum codon, whereby the sequence of codon 10 would depend on the set of nucleotides occupying the wobble positions of the previous nine identifier codons, such that an incorrect codon sequence at codon 10 would indicate a mistake in the decoding of the previous nine identifier codons.

A check-sum value can be selected or determined according to any method known in the art (e.g., barcoding schemes for transmission of data electronically, used to ensure that a transmitted data packet was correct, and to re-send the information if the data was incorrect). In some instances, the value of the nucleotides (where A=0, C=1, G=2 and T=3) used in the sequence can be required to add up to a particular number when a check-sum sequence is added. For example, a four base encode can be anywhere from AAAA to TTTT (or, if written as a sum, 0 to 3333). A value such as 3333 can, for example, be converted to a set of numbers to add (e.g., 3+3+3+3=12). Thus, the set of numbers for any given 6-base sequence in this scheme can be, e.g., required to sum up to 12, where the first 4 bases are the encode and the last 2 bases are the check-sum. For example, if ACGT (0123) is the code, then the checksum would be TT (33), such that the set of numbers reads 012333, which can be converted by the above scheme to 0+1+2+3+3+3=12. In this simplified example, order is not taken into account (e.g., ACGT=TCGA), nor is the fact that ACGT=CCCA. An alternate check-sum scheme can include, for example, a redundancy of bases, so that an encode of, e.g., four bases can be repeated. A check-sum scheme can further include encoding the base-4 (quaternary) sequence of DNA to base-10 (decimal), such that the check-sum can provide a large quantity of information in a reduced coding set. Additional check-sum schemes useful in the methods of the invention are well known in the art.

Maturation

Binding moieties identified by the methods of the present invention may be modified to increase particular binding properties by methods known in the art. For instance, it is beneficial for particular applications that a binding moiety have a $K_D$ less than 10 nM. Methods of improving the properties of antibodies, e.g., methods of affinity maturation, are known in the art.

EXAMPLES

The below exemplary methods shall not limit the scope of the invention as otherwise described above. The below exemplary methods illustrate a subset of the presently invented methods.

Example 1

Identification of a Cognate Binding Moiety of Each of a Plurality of Antigens A population of *E. coli* cells is transfected with a plurality of distinct antigen-encoding plasmids such that the average number of plasmids transfected into each *E. coli* cell is less than one. Each plasmid encodes a fusion protein in which an antigen is fused to F pilin such that expression of the fusion protein in an *E. coli* cell results in display of the antigen on the surface of the cell. The plasmids are all substantially identical in sequence with the exception of the antigen, which varies from plasmid to plasmid. Each plasmid includes the promoter of an ampicillin resistance marker gene positioned immediately adjacent to the sequence encoding the fusion protein. Each plasmid includes an attP site-specific recombination motif positioned immediately adjacent to the sequence encoding the marker gene promoter. Neither the *E. coli* cells nor the plasmid encode a functional ampicillin resistance gene that would be expressed within the *E. coli* cells. The *E. coli* cells are incubated in a manner sufficient to allow expression and display of fusion proteins.

A population of virions is generated such that each virion includes one of a plurality of distinct nucleic acid molecules. Each nucleic acid encodes a fusion protein in which an scFv is fused to a viral transmembrane protein such that the encoded fusion protein may display the scFv on the surface of a virion. Each virus displays a fusion protein encoded by the nucleic acid it includes. The viral nucleic acids are substantially identical in sequence with the exception of the scFv, which may vary from virion to virion. Each nucleic acid additionally includes the coding sequence of an ampicillin resistance marker gene immediately adjacent to the sequence encoding the fusion protein. Each nucleic acid also includes an attB site immediately adjacent to the sequence encoding the ampicillin resistance marker gene. Each of the virions is Gp3-defective. As a result, the virions are inhibited from infecting the *E. coli* cells. This defect may be rescued when an antigen-displayed scFv binds a cell-displayed antigen.

The population of *E. coli* cells is contacted with the population of virions. As a result of the Gp3 defect, cells are selectively infected by virions displaying scFv molecules that bind the antigen displayed by the cell. Recombination may occur between the attP and attB sites. Recombination results in the formation of a recombinant product including a functional ampicillin resistance gene. Accordingly, the population of cells may be incubated in the presence of ampicillin; survival is indicative of infection with subsequent formation of a recombinant product. The recombinant products are isolated from one or more of these cells and sequenced. Each recombinant product includes the sequence of both an antigen and a cognate scFv. As a result, sequencing the recombinant product reveals the sequence of both members of a cognate binding pair.

Example 2

Identification of a Cognate Binding Moiety of Each of a Plurality of Antigens Fused to Gp3

Figure 5:
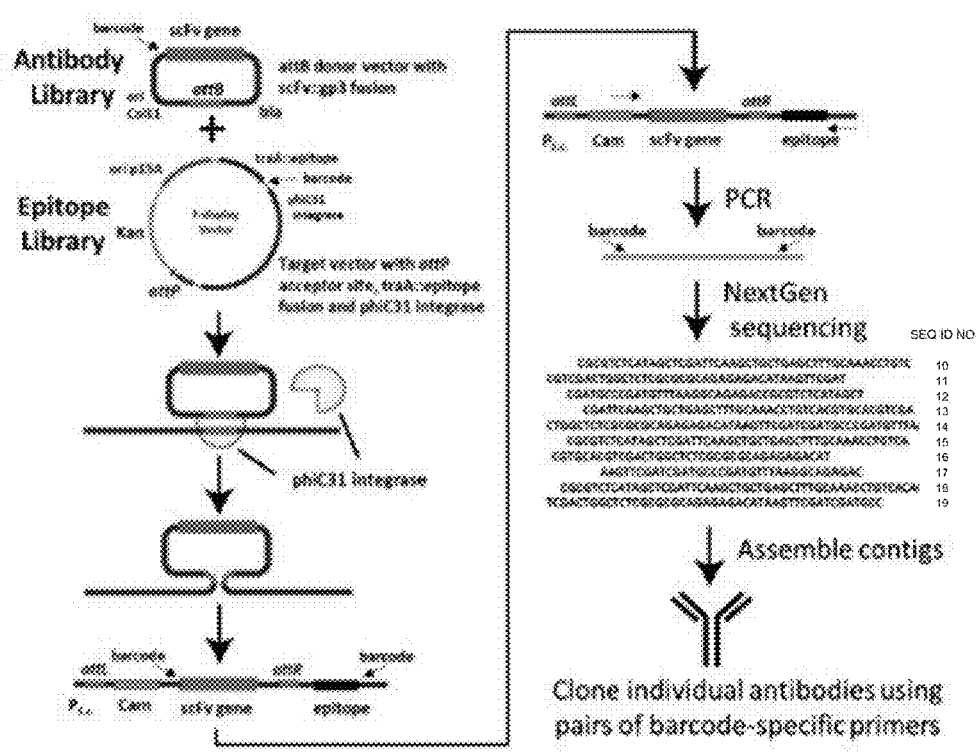
FIG. 5 is a schematic showing recombination between a donor vector having a traA::epitope fusion protein and a target vector within an infected *E. coli* cell, with subsequent steps of amplification and sequencing.

As shown in FIG. 5, each *E. coli* cell of a population of *E. coli* cells includes a vector including a fusion protein in which one of a plurality of antigens (i.e., epitopes) is fused to TraA such that expression of the fusion protein in the *E. coli* cell results in display of the antigen. The nucleic acid vector encoding the antigen further includes a pseudo-attP motif. A pseudo-attP motif is a 34 bp motif that allows unidirectional integration of a circular attB-containing donor vector. The nucleic acid vector encoding the antigen also encodes phiC31 integrase, a sequence-specific serine recombinase capable of facilitating recombination between pseudo-attP and attB site-specific recombination motifs. PhiC31 integrase can integrate a plasmid of any size as a single copy and requires no cofactors. A vector integrated by phiC31 is stably expressed and heritable. In addition, the nucleic acid vector encoding the antigen includes a kanamycin resistance gene (kan) and an *E. coli* promoter capable of promoting expression of a chloramphenicol resistance gene. The promoter capable of promoting expression of a chloramphenicol resistance gene is not operably associated with the coding sequence of a chloramphenicol resistance gene.

Each virion of a population of Gp3-deficient M13 phage virions includes a vector encoding a Gp3 fusion protein including one of a plurality of scFv antibodies such that the encoded fusion protein may display the scFv antibody on the surface of a virion. The scFv vector further encodes a β-lactamase (Bla) enzyme capable of conferring ampicillin resistance, a 34 bp attB motif complementary to a pseudo-attP motif, and the coding sequence of a chlormaphenicol resistance gene that is not operably associated with a promoter.

Each of the antigen vector and the scFv vector further include a variable priming sequence (i.e., barcode). The scFv vector variable priming sequence is adjacent to the 5 terminus of the scFv gene while the antigen vector variable priming sequence is adjacent to the 3' terminus of the epitope gene. Each variable priming sequence includes 6 nucleotides, equivalent to the addition of 2 amino acids. The sequence of each variable priming sequence is a permutation of the sequence: 5'-VDNVDN-3' (where V=A or C or G, D=A or G or T and N=A or C or G or T). The use of VDN codons eliminates both the three stop (TAA, TAG, TGA) and four cysteine (CCN) codons. There are 1,296 possible permutations of VDNVDN is (3×3×4×3×3×4), such that a recombinant product having two bar codes may have any of 1,296^2 (approx. 1.7×10^6) possible pairs of barcode permutations. The sequence of each barcode is determined during gene synthesis.

Binding of a displayed scFv to a displayed antigen may result in infection of the cell displaying the antigen by the virus displaying the scFv. Following infection, the viral vector attB and the antigen vector pseudo-attP site-specific recombination motifs recombine in the presence of phiC31 integrase, which is expressed within the infected cell, resulting in a recombinant product. Site-specific recombination operably associates the coding sequence of the chloramphenicol resistance gene with the *E. coli* promoter capable of promoting expression of the chloramphenicol resistance gene, resulting in a functional chloramphenicol resistance gene (cam), expression of which results in a chloramphenicol resistance phenotype. Absent this site-specific recombination, the cell is not chloramphenicol resistant. The recombinant product is heritable and stably expressed. Accordingly, chloramphenicol resistant cells are selected by incubation of the population of E. coli cells in the presence of chloramphenicol. Recombinant products are isolated from the pool of chloramphenicol resistant cells.

PCR is used to amplify a segment of one or more isolated recombinant products. Each segment includes at least a portion of the sequence encoding a scFv and at least a portion of the sequence encoding an antigen, as well as an antigen vector variable priming sequence and a scFv vector variable priming sequence. In particular, the polynucleotide sequence between the 5 side of the scFv gene and the 3' side of the antigen is amplified. The amplified segment is sequenced by a Next Generation sequencing technology, such as Illumina or 454 sequencing, using a primer-walking strategy. Contigs are assembled from the sequencing reads. After contig assembly, individual sequences are differentiated by variable priming sequences included in the antibody and antigen constant regions. Segments having particular variable priming sequences are selectively amplified using oligonucleotide pairs capable of hybridizing to the variable priming sequences and sub-cloned into an expression system.

Example 3

Figure 6:
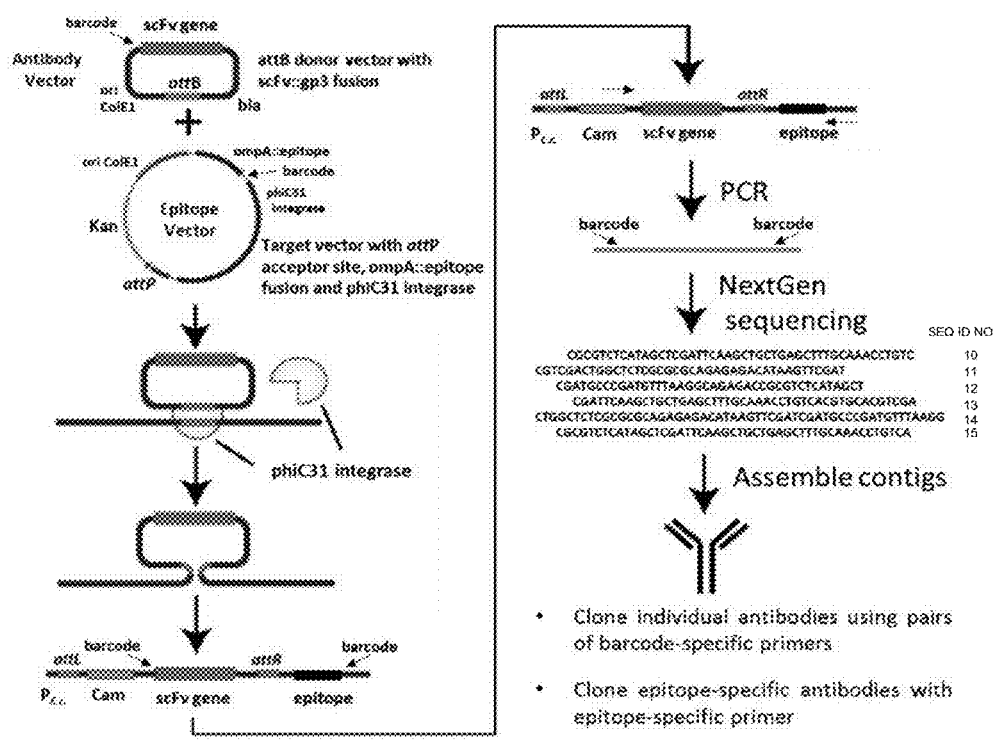
FIG. 6 is a schematic showing recombination between a donor vector having an ompA::epitope fusion protein and a target vector within an infected *E. coli* cell, with subsequent steps of amplification and sequencing.

Identification of a Cognate Binding Moiety of Each of a Plurality of Antigens Fused to OmpA As shown in FIG. 6, each E. coli cell of a population of E. coli cells includes a vector including a fusion protein in which one of a plurality of antigens (i.e., epitopes) is fused to OmpA, such that expression of the fusion protein in E. coli cell results in display of the antigen. The nucleic acid vector encoding the antigen further includes a pseudo-attP motif. A pseudo-attP motif is a 34 bp motif that allows unidirectional integration of a circular attB-containing donor vector. The nucleic acid vector encoding the antigen also encodes phiC31 integrase, a sequence-specific serine recombinase capable of facilitating site-specific recombination between pseudo-attP and attB site-specific recombination motifs. PhiC31 integrase can integrate a plasmid of any size as a single copy and requires no cofactors. A vector integrated by phiC31 is stably expressed and heritable. In addition, the nucleic acid vector encoding the antigen includes a kanamycin resistance gene (kan) and an E. coli promoter capable of promoting expression of a chloramphenicol resistance gene. The promoter capable of promoting expression of a chloramphenicol resistance gene is not operably associated with the coding sequence of a chloramphenicol resistance gene.

Each virion of a population of Gp3-deficient M13 phage virions includes a vector encoding a Gp3 fusion protein including one of a plurality of scFv antibodies such that the encoded fusion protein can display the scFv antibody on the surface of a virion. The scFv vector further encodes a β-lactamase (Bla) enzyme capable of conferring ampicillin resistance, a 34 bp attB motif complementary to a pseudo-attP motif, and the coding sequence of a chlormaphenicol resistance gene that is not operably associated with a promoter.

Each of the antigen vector and the scFv vector further include a variable priming sequence (i.e., barcode). The scFv vector variable priming sequence is adjacent to the 5 terminus of the scFv gene while the antigen vector variable priming sequence is adjacent to the 3' terminus of the antigen gene. Each variable priming sequence includes 6 nucleotides, equivalent to the addition of 2 amino acids. The sequence of each variable priming sequence is a permutation of the sequence: 5'-VDNVDN-3' (where V=A or C or G, D=A or G or T and N=A or C or G or T). The use of VDN codons eliminates both the three stop (TAA, TAG, TGA) and four cysteine (CCN) codons. There are 1,296 possible permutations of VDNVDN is (3×3×4×3×3×4), such that a recombinant product having two bar codes can have any of 1,296^2 (approx. 1.7×10^6) possible pairs of barcode permutations. The sequence of each barcode is determined during gene synthesis.

Binding of a displayed scFv to a displayed antigen may result in infection of the cell displaying the antigen by the virus displaying the scFv. Following infection, the viral vector attB and the antigen vector pseudo-attP site-specific recombination motifs recombine in the presence of phiC31 integrase, which is expressed within the infected cell, resulting in a recombinant product. Site-specific recombination operably associates the coding sequence of the chloramphenicol resistance gene with the E. coli promoter capable of promoting expression of the chloramphenicol resistance gene, resulting in a functional chloramphenicol resistance gene (cam), expression of which results in a chloramphenicol resistance phenotype. Absent this site-specific recombination, the cell is not chloramphenicol resistant. The recombinant product is heritable and stably expressed. Accordingly, chloramphenicol resistant cells are selected by incubation of the population of E. coli cells in the presence of chloramphenicol. Recombinant products are isolated from the pool of chloramphenicol resistant cells.

PCR is used to amplify a segment of one or more isolated recombinant products. Each segment includes at least a portion of the sequence encoding a scFv and at least a portion of the sequence encoding an antigen, as well as an antigen vector variable priming sequence and a scFv vector variable priming sequence. In particular, the polynucleotide sequence between the 5' side of the scFv gene and the 3' side of the antigen is amplified. The amplified segment is sequenced by a Next Generation sequencing technology, such as Illumina or 454 sequencing, using a primer-walking strategy. Contigs are assembled from the sequencing reads. After contig assembly, individual sequences are differentiated by variable priming sequences included in the antibody and antigen constant regions. Segments having particular variable priming sequences are selectively amplified using oligonucleotide pairs capable of hybridizing to the variable priming sequences and sub-cloned into an expression system.

Example 4

Figure 7:
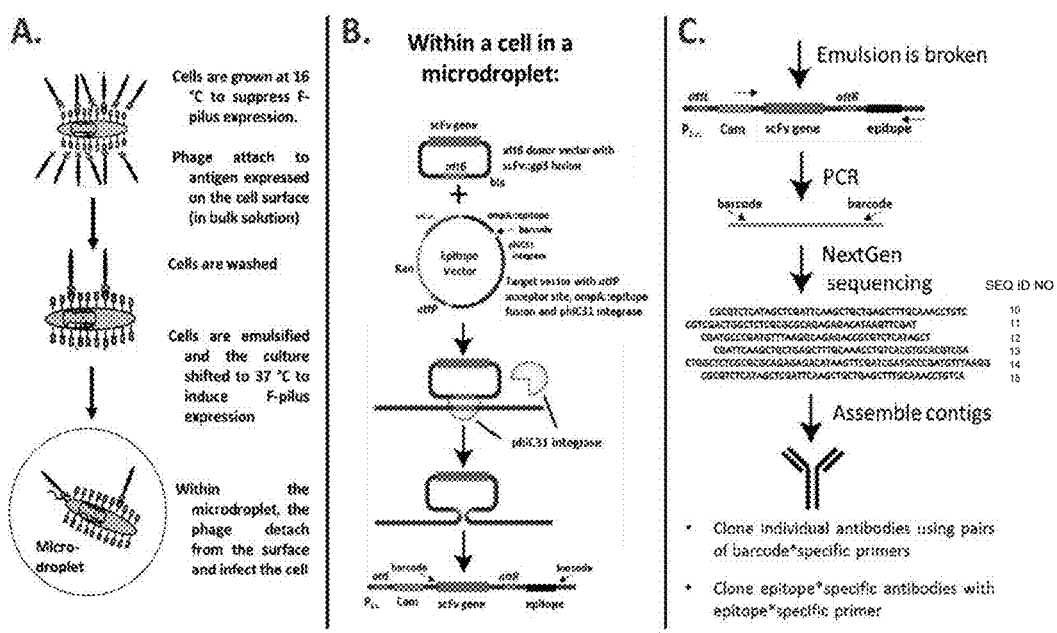
FIGS. 7A-C are schematics showing recombination between a donor vector having an ompA::epitope fusion protein and a target vector within an infected *E. coli* cell after a conditional infection step, with subsequent steps of amplification and sequencing.

Identification of a Cognate Binding Moiety of Each of a Plurality of Antigens Fused to OmpA and Displayed by Infection-Defective Virions As shown in FIGS. 7A-C, each E. coli cell of a population of E. coli cells includes a vector including a fusion protein in which one of a plurality of antigens (i.e., epitopes; approximately $10^4$ antigens) is fused to OmpA such that expression of the fusion protein in the E. coli cell results in display of the antigen. The nucleic acid vector encoding the antigen further includes a pseudo-attP motif. A pseudo-attP motif is a 34 bp motif that allows unidirectional integration of a circular attB-containing donor vector. The nucleic acid vector encoding the antigen also encodes phiC31 integrase, a sequence-specific serine recombinase capable of facilitating site-specific recombination between pseudo-attP and attB site-specific recombination motifs. PhiC31 integrase can integrate a plasmid of any size as a single copy and requires no cofactors. A vector integrated by phiC31 is stably expressed and heritable. In addition, the nucleic acid vector encoding the antigen includes a kanamycin resistance gene (kan) and an *E. coli* promoter capable of promoting expression of a chloramphenicol resistance gene. The promoter capable of promoting expression of a chloramphenicol resistance gene is not operably associated with the coding sequence of a chloramphenicol resistance gene. Each *E. coli* cell expresses the F pilus (F$^+$ phenotype) or not (F$^-$ phenotype) in a temperature-dependent manner. At 16° C. the cells do not express the F pilus, but at 37° C. the F pilus is expressed.

Each virion of a population of Gp3-deficient M13 phage virions includes a vector encoding a Gp3 fusion protein including one of a plurality of scFv antibodies (approximately $10^{10}$ or more antibodies) such that the encoded fusion protein can display the scFv antibody on the surface of a virion. The scFv vector further encodes a β-lactamase (Bla) enzyme capable of conferring ampicillin resistance, a 34 bp attB motif complementary to a pseudo-attP motif, and the coding sequence of a chlormaphenicol resistance gene that is not operably associated with a promoter. Because the M13 bacteriophage requires the presence of an F pilus, the virions are infection deficient with respect F$^-$ *E. coli* cells, even when an antigen binds with an scFv.

Each of the antigen vector and the scFv vector further include a variable priming sequence (i.e., barcode). The scFv vector variable priming sequence is adjacent to the 5 terminus of the scFv gene while the antigen vector variable priming sequence is adjacent to the 3' terminus of the epitope gene. Each variable priming sequence includes 6 nucleotides, equivalent to the addition of 2 amino acids. The sequence of each variable priming sequence is a permutation of the sequence: 5'-VDNVDN-3' (where V=A or C or G, D=A or G or T and N=A or C or G or T). The use of VDN codons eliminates both the three stop (TAA, TAG, TGA) and four cysteine (CCN) codons. There are 1,296 possible permutations of VDNVDN is (3×3×4×3×3×4), such that a recombinant product having two bar codes can have any of 1,296^2 (approx. 1.7×10^6) possible pairs of barcode permutations. The sequence of each barcode is determined during gene synthesis.

The cells and virions are contacted and incubated in bulk solution at 16° C. in a manner sufficient to allow binding of one or more displayed scFv binding moieties to one or more displayed antigens. Infection does not occur at this step. The cells and virions are washed to remove unbound or poorly bound virions. Subsequently, the remaining cells and virions are emulsified in a water-in-oil emulsion. Emulsion results in the formation of droplets, each droplet potentially including a cell displaying an antigen bound by a virion displaying a cognate binding moiety via cognate pair binding. Each droplet of the emulsion may include on average, rounded to the nearest whole number, 1 cell. The emulsion further includes TEV protease to cleave the antibody from the Gp3 protein. The emulsion is incubated in a manner sufficient to allow cleavage of one or more antigens or one or more cognate binding moieties. The emulsion is incubated at 37° C., allowing expression of the F pilus. Expression of the F pilus cures the infection deficiency of the virions, allowing infection of one or more cells present in an emulsion droplet by one or more virions present in the same droplet.

Following infection, the viral vector attB and the antigen vector pseudo-attP site-specific recombination motifs recombine in the presence of phiC31 integrase, which is expressed within the infected cell, resulting in a recombinant product. Site-specific recombination operably associates the coding sequence of the chloramphenicol resistance gene with the *E. coli* promoter capable of promoting expression of the chloramphenicol resistance gene, resulting in a functional chloramphenicol resistance gene (cam), expression of which results in a chloramphenicol resistance phenotype. Absent this site-specific recombination, the cell is not chloramphenicol resistant. The recombinant product is heritable and stably expressed. Accordingly, chloramphenicol resistant cells are selected by incubation of the population of *E. coli* cells in the presence of chloramphenicol. Following incubation, plates are scraped to pool resistant colonies. Recombinant products are isolated from the pool of chloramphenicol resistant cells.

PCR is used to amplify a segment of one or more isolated recombinant products. Each segment includes at least a portion of the sequence encoding a scFv and at least a portion of the sequence encoding an antigen, as well as an antigen vector variable priming sequence and a scFv vector variable priming sequence. In particular, the polynucleotide sequence between the 5 side of the scFv gene and the 3' side of the antigen is amplified. Antibodies against a specific epitope can be amplified using an epitope-specific oligonucleotide primer. Amplified segments are sequenced by a Next Generation sequencing technology, such as Illumina or 454 sequencing, using a primer-walking strategy. Contigs are assembled from the sequencing reads. After contig assembly, individual sequences are differentiated by variable priming sequences included in the antibody and antigen constant regions. Specific antibodies can be amplified by oligonucleotide primers targeting particular pairs of variable priming sequence permutations. Amplified segments are sub-cloned into an expression system.

Example 5

Identification of a Cognate Binding Moiety of Each of 12 *Burkholderia pseudomallei* Antigens Fused to OmpA and Displayed by Infection-Defective Virions An antigen library including four *Burkholderia pseudomallei* proteins known to contribute to virulence and/or predicted to be displayed by *Burkholderia pseudomallei* is assembled. The antigen library includes two *Burkholderia pseudomallei* flagellin protein fragments, the capsular antigen, and acid phosphatase. In addition, for each of the four proteins, two overlapping 30 amino acid fragments are included in the library. The two fragments of each protein overlap by 15 amino acids. A nucleic acid sequence encoding each antigen is cloned into an Lpp-OmpA vector for expression in an Lpp-OmpA fusion protein. The antigen fusion proteins are displayed in *E. coli*. Each antigen is additionally separately fused to the maltose-binding protein MBP for protein purification.

An scFv binding moiety library is constructed by fusing each of a plurality of scFv binding moieties to a Gp3 protein of M13. The library includes greater than >$10^{10}$ binding moiety fusion proteins. Binding moiety fusion proteins are displayed by M13 bacteriophage.

Antigen-displaying cells are contacted with scFv displaying virions in bulk and incubated at 16° C. with suitable aeration. After 10 minutes, the cells (and any adsorbed phage) are pelleted by centrifugation and the phage remaining in solution are washed away. The cells are resuspended, emulsified in perfluorocarbon oils, and incubated at 37° C. for 60 minutes or a period of time otherwise determined to permit infection and recombination. A cam$^R$ gene is selectively expressed by cells in which infection and recombination have occurred (see, e.g., Example 4). Recombinant products include two barcodes (see, e.g., Example 4). Following incubation at 37° C., cells are plated on Cam-selective media. Recombinant products from cam$^R$ cells are pooled and amplified by PCR and the pooled sample is submitted to paired-end sequencing on an ILMN HiSeq instrument. DNA analysis performed using DNAStar Lasergene software is used to associate the barcodes with an antigen and a cognate binding moiety. If needed, primer walking can be utilized to sequence the entire length of amplified segments. Sequencing results are analyzed by comparison to data derived from the next generation sequencing.

Following the identification of cognate pairs encoded by recombinant products of cam$^R$ cells, particular scFv sequences are selectively amplified using oligonucleotide pairs that include at least one oligonucleotide complementary to a barcode associated with the particular scFv sequence. The PCR-amplified antibody genes are subcloned into a pAPIII-6 vector under the control of the phoA promoter. The scFv proteins are expressed and purified. The resulting protein includes an N-terminal FLAG and C-terminal His-tag for detection and purification purposes. Purified scFv proteins are evaluated by Western analysis and immunofluorescence against *E. coli* cells expressing the target antigen as a TraA fusion protein.

Biopanning procedures known in the art will be used to validate identified scFv antibodies. 384 clones are tested by phage-ELISA against the screened MBP-antigens, as well as a negative control protein. ELISA-positive clones are analyzed by next generation sequencing.

Controls include data collected using a naïve phage library and selection for scFv antibodies against any single antigen of the antigen library. Sequences common to multiple control pools representing selection against any one of the 12 antigens of the antigen library alone, in particular common to unrelated antigens or antigen fragments, are subtracted. However, an scFv antibody exclusively shared by a set of three antigens derived from a single protein is an scFv that binds to a region shared by the three antigens. Identified scFv antibodies are amplified by oligonucleotide primer pairs that include, e.g., an epitope-specific oligonucleotide and an scFv-flanking oligonucleotide or oligonucleotides specific to variable priming sequences that flank the scFv sequence. Amplified scFv antibodies are subcloned into a pAPIII-6 vector under the control of the phoA promoter and the scFv is expressed and purified. The resulting protein has an N-terminal FLAG and C-terminal HIS-tag for, e.g., detection and purification. Purified scFv antibodies are evaluated in Western analysis and immunofluorescence techniques against *E. coli* cells expressing the targeted epitope.

Example 6

Identification of a Cognate Binding Moiety of Each of a Plurality of *Burkholderia Pseudomallei* Antigens Fused to OmpA and Displayed by Infection-Defective Virions An antigen library including ten *Burkholderia pseudomallei* proteins known to contribute to virulence and/or predicted to be displayed by *Burkholderia pseudomallei* is assembled. The antigen library also includes *Burkholderia pseudomallei* flagellin protein fragments, capsular antigens, and acid phosphatase. The selected antigens are analyzed by BLASTp against the *E. coli* proteome. Antigens having high homology to any *E. coli* protein are eliminated from further analysis. Additional antigens are selected by dividing a subset of the selected proteins into 30 amino acid fragments by dividing the amino acid sequence of the protein at 15 amino acid increments. For instance, a protein having 90 amino acids is divided, e.g., into fragments including amino acids 1-30, 15-45, 30-60, 45-75, and 60 to 90. A nucleic acid sequence encoding each antigen is cloned into an ompA vector for expression in an OmpA fusion protein. The antigen fusion proteins are displayed in *E. coli*.

An scFv binding moiety library is constructed by fusing each of a plurality of scFv binding moieties to a Gp3 protein of M13. The library includes greater than >10$^{10}$ binding moiety fusion proteins. Binding moiety fusion proteins are displayed by M13 bacteriophage.

Antigen-displaying cells are contacted with scFv displaying virions in bulk and incubated at 16° C. with suitable aeration. After 10 minutes, the cells (and any adsorbed phage) are pelleted by centrifugation and the phage remaining in solution are washed away. The cells are resuspended, emulsified in perfluorocarbon oils, and incubated at 37° C. for 60 minutes or a period of time otherwise determined to permit infection and recombination. A cam$^R$ gene is selectively expressed by cells in which infection and recombination have occurred (see, e.g., Example 4). Recombinant products include two barcodes (see, e.g., Example 4). Following incubation at 37° C., cells are plated on Cam-selective media. Recombinant products from cam$^R$ cells are pooled and amplified by PCR and the pooled sample is submitted to paired-end sequencing on an ILMN HiSeq instrument. DNA analysis performed using DNAStar Lasergene software is used to associate the barcodes with an antigen and a cognate binding moiety. If needed, primer walking is utilized to sequence the entire length of amplified segments. Sequencing results are analyzed by comparison to data derived from the next generation sequencing.

Following the identification of cognate pairs encoded by recombinant products of cam$^R$ cells, particular scFv sequences are selectively amplified using oligonucleotide pairs that include at least one oligonucleotide complementary to a barcode associated with the particular scFv sequence. The PCR-amplified antibody genes are subcloned into a pAPIII-6 vector under the control of the phoA promoter. The scFv proteins are expressed and purified. The resulting protein includes an N-terminal FLAG and C-terminal His-tag for detection and purification purposes. Purified scFv proteins are evaluated by Western analysis and immunofluorescence against *E. coli* cells expressing the target antigen as a TraA fusion protein.

Example 7

Increased Transformation Efficiency and Recombinant Rate with the Use of AXE688 Cells The Eco29k I restriction endonuclease is a Sac II isoschizomer that recognizes the sequence 5'-CCGCGG-3' and is encoded, along with the Eco29k I methylase, in the *Escherichia coli* strain 29k. We expressed the Eco29k I restriction-methylation system in *E. coli* strain TG1 to produce the strain AXE688. We also developed a directed molecular evolution mutagenesis method that uses Eco29k I to restrict incoming parental DNA in transformed cells. Using our method, termed AXM mutagenesis, a large, mutated DNA fragment is produced using PCR conditions that promote nucleotide misincorporation into newly synthesized DNA.

To determine whether Eco29k I could enhance the efficiency of the AXM mutagenesis method, electrocompetent cells were generated from the AXE688 strain. In other instances, alternate strains capable of restricting incoming DNA can be used (e.g., a strain expressing DpnI, which can restrict modified DNA, or a strain expressing Sau3AI, which can restrict unmodified DNA). Indeed, any method of distinguishing old and new DNA can be used in the methods of the invention. The electroporation efficiencies of the AXE688 cells and standard TG1 cells using pUC19 DNA (which does not contain an Eco29k I site) are equivalent (Table 1).

TABLE 1

Electroporation efficiency of strain AXE688 and TG1.

| Strain | Efficiency (cfu/ug)[1] |
|---|---|
| TG1 | $2.5 \times 10^{10}$ |
| AXE688 | $1.5 \times 10^{10}$ |

[1]Efficiencies were based on the number of ampicillin-resistant colonies after transformation with 0.01 ng of pUC19 DNA.

To evaluate the transformation efficiency of the AXE688 cells when one plasmid contains Eco29k I sites, we mixed the two plasmids described above, one lacking Eco29k I sites and one containing six Eco29k I sites, at various ratios. Equal amounts (100 ng) of the plasmid mixtures were transformed into either TG1 or AXE688 cells. The transformation efficiencies of TG1 and AXE688 cells were nearly equivalent ($5.8 \times 10^9$ and $3.6 \times 10^9$ cfu/µg, respectively) when 100% of the input plasmid lacked Eco29k I sites (Table 2).

TABLE 2

Recovery of mixtures of plasmids with and without Eco29k I sites in TG1 and AXE688 cells.

| Strain | Input Ratio Eco29k I +/ Eco29k I − | Transformation efficiency (cfu/µg) | Recovered clones (% Eco29k I −) |
|---|---|---|---|
| TG1 | 0/100 | $5.8 \times 10^9$ | 100 |
| TG1 | 50/50 | $1.1 \times 10^{10}$ | 29 |
| TG1 | 90/10 | $1.1 \times 10^{10}$ | 8 |
| TG1 | 100/0 | $1.25 \times 10^{10}$ | 0 |
| AXE688 | 0/100 | $3.6 \times 10^9$ | 100 |
| AXE688 | 50/50 | $2.4 \times 10^9$ | >96 |
| AXE688 | 90/10 | $7 \times 10^8$ | >96 |
| AXE688 | 100/0 | $1.2 \times 10^5$ | NA |

As expected, the efficiency went down >10,000-fold in AXE688 when 100% of the input plasmid contained Eco29k I sites (Table 2). Although the transformation efficiency in TG1 remained constant with the different input plasmid mixtures, the frequency of clones lacking Eco29k I sites closely matched the frequency of the vector lacking Eco29k I sites in the input mixture (Table 2; 29% for the 50:50 mixture and 8% for the 90:10 mixture of Eco29k I site-containing vector to Eco29k I site-lacking vector). In contrast, although the transformation efficiency was slightly reduced in AXE688 when 90% of the input mixture contained Eco29k I sites, greater than 96% of the recovered clones lacked the Eco29k I site (Table 2). These results suggested that the AXE688 cells could be used to create libraries of nearly 100% recombinant clones. A dsDNA heteroduplex library product generated using the AXM mutagenesis method on several different starting scFvs was transformed either into AXE688 or TG1 competent cells, and the number of recombinant clones was determined by DNA sequencing (Table 3).

TABLE 3

Use of restriction endonuclease in vivo reduces parental clones in affinity maturation libraries.

| | | TG1 | | AXE688 | |
|---|---|---|---|---|---|
| EP PCR Template | Phagemid Template[1] | % Recombinants | Transformation Efficiency (cfu/µg) | % Recombinants | Transformation Efficiency (cfu/µg) |
| scFv 1 | Eco29k I | 40 | $3.7 \times 10^8$ | 89 | $6.6 \times 10^8$ |
| scFv 2 | Eco29k I | 6 | $3.2 \times 10^8$ | 94 | $8.7 \times 10^7$ |
| scFv 3 | Eco29k I | 31 | $8 \times 10^8$ | 100 | $4.3 \times 10^8$ |
| scFv 3 | no RE sites | 30 | $5.7 \times 10^8$ | 29 | $8.7 \times 10^8$ |

[1]The circular, single-stranded phagemid template either contains or lacks Eco29k I sites in the scFv CDRs.

The number of recombinants, e.g., clones with fully incorporated error-prone PCR product, varied from 6 to 40% when the heteroduplex product was transformed into standard TG1 cells. However, when the scFv libraries were transformed into the AXE688 strain expressing Eco29k I, 90% or more of recovered clones were non-parental (e.g., containing no Eco29k I sites) (Table 3). Since the recombinant clones do not contain Eco29k I sites in the CDRs, they are not affected by the Eco29k I endonuclease activity. The increased frequency of recombinants in AXE688 is dependent on restriction of DNA containing Eco29k I sites because when the vector template used for Kunkel mutagenesis lacks Eco29k I sites, little difference in the number of recombinants is observed between the standard TG1 and AXE688 cells. The actual number of transformants more closely represents the true library size in the AXE688 strain (Table 3).

Similar to the AXM mutagenesis libraries, when the standard Kunkel library (incorporating randomized oligonucleotides at 4 CDRs) was transformed into AXE688 cells, greater than 95% of the resultant clones were recombinant versus 8% in TG1 (Table 4). These results demonstrate that the AXE688 strain enables the construction of phage display libraries that have a higher (>90%) frequency of recombinant clones than typically achieved by Kunkel mutagenesis alone. These libraries with high diversity and functionality can be generated without the requirement for time consuming and labor intensive in vitro processing steps.

TABLE 4

Use of restriction endonuclease in vivo reduces parental clones in naïve library.

| | | TG1 | | AXE688 | |
|---|---|---|---|---|---|
| # mutagenic oligos[1] | ssDNA template[2] | % Non-parentals | Transformation Efficiency (cfu/μg) | % Non-parentals | Transformation Efficiency (cfu/μg) |
| 4 | Eco29k I | 8 | $1.1 \times 10^9$ | 96 | $2.3 \times 10^8$ |

[1]Oligonucleotides containing "NNK" nucleotides at variable positions in four of the CDRs of the scFv were generated.
[2]The circular, single-stranded phagemid template contains Eco29k I sites in the 4 CDRs targeted for mutagenesis.

Example 8

F Pilus Formation is Suppressed at 16° C.

Figure 8:
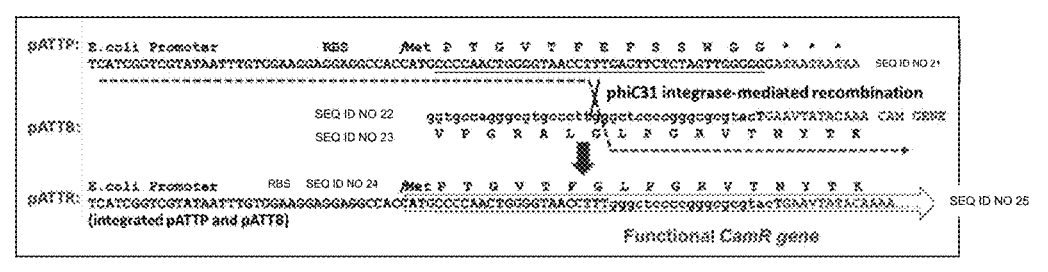
Figure 9:
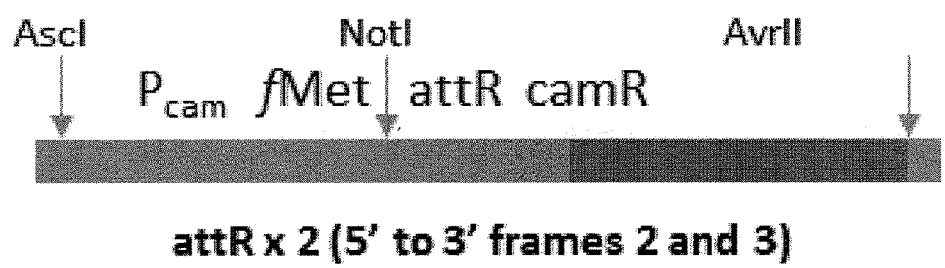
FIG. 9 is a schematic showing a design for the $Cm^R$ cassette with phiC31 integrase attR site in frame with the gene. A NotI site was incorporated immediately downstream of the initiating methionine (fMet) for the $Cm^R$ gene. Downstream of the NotI site, the phiC31 integrase attR sequence was fused in frame (5' to 3' frames 2 and 3) to the $Cm^R$ gene.
Figure 10:
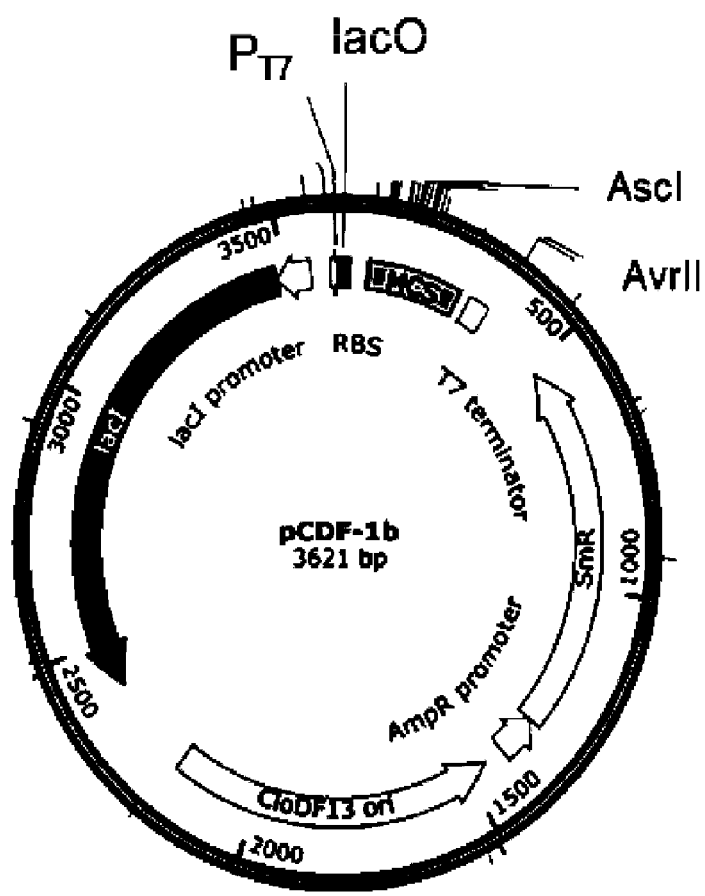
FIG. 10 is a schematic showing a map of pCDF-1b. The $Cm^R$ cassette was cloned into the AscI and AvrII sites of the plasmid pCDF-1b.

The *E. coli* strain TG1 [F' (traD36, proAB+ lacI$^q$, lacZΔM15), supE, thi-1, Δ(lac-proAB), Δ(mcrB-hsdSM)5, (rK$^-$mK$^-$)] was purchased from Lucigen (Middleton, Wis.). The expression cassette for the chloramphenicol resistance gene (Cm$^R$) was derived from the sequence of the gene and promoter in pACYC184 (New England Biolabs). A Not I site was added immediately downstream of the initiating methionine (fMet). Three variants of the chloramphenicol resistance cassette were generated. One variant contained the wild type cassette incorporating the Not I site only. A second contained the phiC31 integrase attR sequence (FIG. 8) in 5' to 3' reading frame 2 (Table 5) downstream of the Not I site and in frame with the Cm$^R$ gene ORF. The third variant contained the phiC31 integrase attR sequence in 5' to 3' reading frame 3 (Table 5) downstream of the Not I site and in frame with the CmR gene ORF. The expression vector for chloramphenicol resistance was made by cloning the synthesized constructs (FIG. 9) between the Asc I and Avr II sites in pCDF-1b (Novagen, MA; FIG. 10). The pCDF-1b plasmid uses the CloDF13 origin of replication and is compatible with ColE1 plasmids. This vector also contains a spectinomycin resistance gene.

TABLE 5

Amino acid sequences encoded by phiC31 integrase attR site.

| Reading Frame | Sequence |
|---|---|
| 5' to 3' Fr2 | PNWGNLWAPRAR (SEQ ID NO: 27) |
| 5' to 3' Fr3 | PTGVTFGLPGRV (SEQ ID NO: 28) |

To test the functionality of the chloramphenicol resistance gene, the three plasmid variants were transformed into TG1 cells and transformants were selected on LB-agar plates containing spectinomycin (50 μg/ml). Spectinomycin-resistant colonies were streaked onto fresh LB-agar plates containing chloramphenicol (33 μg/ml). Colonies derived from all three vector variants were able to grow on chloramphenicol-containing plates, indicating that the attR sequence did not affect the functionality of the chloramphenicol resistance gene.

Figure 11:
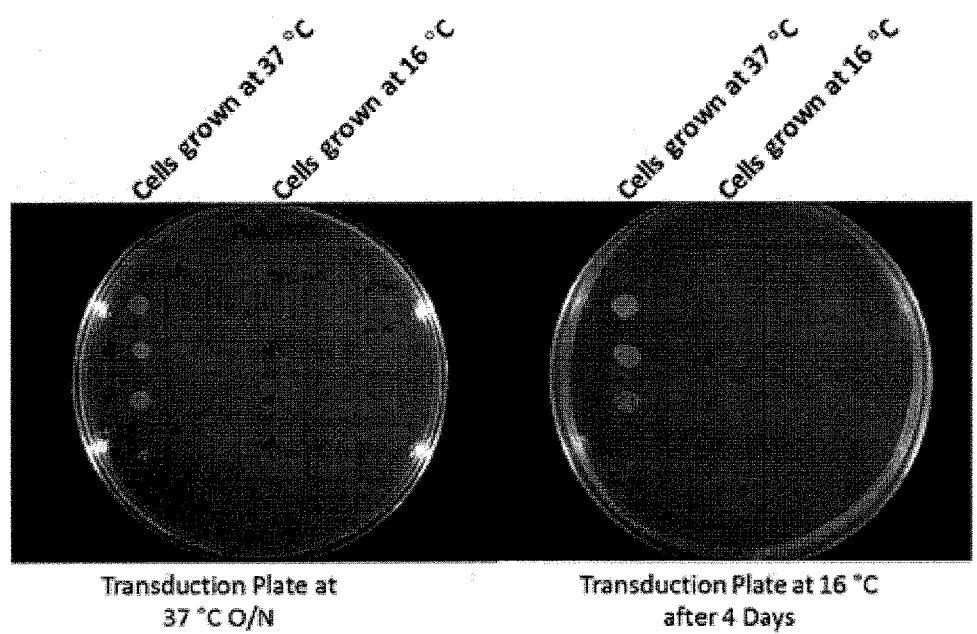
FIG. 11 is an image showing phage transduction at 37° C. and 16° C. Colonies are observed on plates incubated at both 37° C. and 16° C. if cells were grown at 37° C. prior to phage transduction. No colonies are observed on plates incubated at either 37° C. or 16° C. if cells were grown at 16° C. prior to phage transduction.

TG1 cells were struck out on an LB-agar plate for single colony isolation. A single colony was used to inoculate 1 ml of LB media in a 14-ml snap cap tube. The culture was incubated at either 37° C. or 16° C. with shaking until the cells reached mid-log phase (OD$_{600}$=0.4). Bacteriophage M13 (20 μl; ~$2 \times 10^9$) that had packaged an ampicillin-resistant phagemid was incubated with the mid-log phase cells (600 μl; ~$2 \times 10^8$) at 37° C. or 16° C. for 30 minutes without shaking. The cells were then washed 3 times with PBS followed by one time with LB media. Serial dilutions of the cells were plated on LB-agar plates containing ampicillin. The plates were incubated at either 37° C. or 16° C. If the cells were grown at 37° C. prior to phage transduction, colonies were observed on the plates at both temperatures (FIG. 11). However, if the cells were grown at 16° C. prior to phage transduction, no colonies were observed on plates incubated at either 37° C. or 16° C. (FIG. 11). This result shows that F pilus formation is suppressed at 16° C.

Other Embodiments

All publications, patent applications, and patents mentioned in this specification are herein incorporated by reference.

While the invention has been described in connection with the specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A method of isolating a cognate binding moiety of one or more antigens, said method comprising the steps of:
   a) providing
      1) a population of cells, each of said cells comprising:
         i) a cell surface antigen and
         ii) a nucleic acid comprising a first recombination motif, and
      2) a plurality of attachment-defective virions, each of said virions comprising:
         i) one of a plurality of transgenic viral surface binding moieties and
         ii) a nucleic acid comprising a second recombination motif capable of integrating with said first motif;
   b) contacting said population of cells with said virions, wherein, if one or more of said virions comprise a cognate binding moiety of one or more of said cell surface antigens, binding of said cell surface antigen and said cognate binding moiety results in selective infection by the bound virion of the cell comprising said cell surface antigen of said cognate binding moiety;
   c) incubating said population of cells under conditions sufficient to allow recombination between said first and second recombination motifs in infected cells, thereby generating a recombinant product; and
   d) isolating the recombinant product, thereby by isolating the cognate binding moiety.

2. The method of claim 1, wherein:

(i) said cell comprises a recombination enzyme, preferably wherein said recombination enzyme is an integrase;

(ii) the nucleic acid comprised by one or more of said virions encodes a recombination enzyme and said incubation is sufficient to allow expression of said encoded recombination enzyme, preferably wherein said recombination enzyme is an integrase;

(iii) one or more of said recombination motifs is a site-specific recombination motif;

(iv) each of said cells comprises one of a plurality of distinct cell surface antigens; and/or (v) one or more of said cell surface antigens are transgenic.

3. The method of claim 1, wherein the method is a method of isolating a cognate binding moiety of each of a plurality of antigens, and wherein:

step a) comprises providing 1) a population of cells, each of said cells comprising:

i) one of a plurality of transgenic cell surface antigens, ii) a nucleic acid comprising a first marker gene fragment adjacent to a first site-specific recombination motif, and iii) a recombination enzyme, and 2) a plurality of attachment-defective virions, each of said virions comprising:

i) one of a plurality of transgenic viral surface binding moieties and ii) a nucleic acid comprising a second marker gene fragment adjacent to a second site-specific recombination motif capable of integrating with said first motif, wherein said first marker gene fragment and said second marker gene fragment are positioned such that site-specific recombination between said first and second motif will result in a functional marker gene;

step c) comprises incubating said population of cells under conditions sufficient to allow site-specific recombination between said first and second site-specific recombination motifs in infected cells, thereby generating a recombinant product capable of expressing a functional marker protein;

incubating said population of cells in a manner sufficient to allow detection of cells having a phenotype resulting from expression of said functional marker protein; and step d) comprises isolating one or more cells having said detectable phenotype.

4. The method of claim 3, wherein:

(i) one or more of said first marker gene fragments or one or more of said second marker gene fragments comprise a functional marker gene promoter and one or more of said first marker gene fragments or one or more of said second marker gene fragments comprise a coding segment of the same functional marker gene;

(ii) said marker gene is an antibiotic resistance gene;

(iii) said marker gene encodes a fluorescent protein;

(iv) the polynucleotide sequence of one or more of said transgenic cell surface antigens is adjacent to a first marker gene fragment;

(v) the polynucleotide sequence of one or more of said transgenic viral surface binding moieties is adjacent to a second marker gene fragment; and/or (vi) said recombination enzyme is an integrase.

5. The method of claim 4, wherein:

(i) one of said first marker gene fragment or said second marker gene fragment comprises a promoter gene fragment and the other comprises a coding gene fragment; or (ii) one of said first marker gene fragment or said second marker gene fragment comprises a promoter gene fragment and a 5' coding gene fragment and the other comprises a 3' coding gene fragment.

6. The method of claim 1, wherein:

(i) one or more of said transgenic cell surface antigens are comprised by a cell surface antigen fusion protein;

(ii) one or more of said transgenic viral surface binding moieties are viral surface binding moiety fusion proteins;

(iii) said cells are bacterial, yeast, or mammalian cells;

(iv) said virions are attachment-defective bacteriophage, baculovirus, or adenovirus virions;

(v) said virions are M13 phage lacking Gp3;

(vi) said first and second recombination motifs are att recombination motifs;

(vii) said population of cells comprises a plurality of transgenic cell surface antigens comprising 10,000or more distinct antigens; and/or (viii) said plurality of transgenic viral surface binding moieties comprises 10,000 or more distinct binding moieties.

7. The method of claim 1, wherein said antigen comprises one or more modified amino acids.

8. The method of claim 7, wherein one or more of said modified amino acids are phosphoserines.

9. The method of claim 1, wherein:

(i) one or more of said binding moieties are antibodies; and/or (ii) one or more of said binding moieties are scFv binding moieties.

10. The method of claim 1, wherein:

(i) one or more of said viral surface binding moieties comprise one or more segments derived from the sequence of an antibody expressed by a cell of an inoculated subject; and/or (ii) one or more of said viral surface binding moieties comprise one or more segments derived from the sequence of an antibody expressed by a na ïve cell.

11. The method of claim 1, wherein one or more of said antigens is an antigen isolated from a pathogen.

12. The method of claim 1, wherein:

(i) said recombinant product comprises one or more variable priming sequences;

(ii) said recombinant product comprises two variable priming sequences that flank the sequences of said antigen and said binding moiety.

13. The method of claim 1, wherein step (b) further comprises emulsifying the population of cells and said bound virions, thereby encapsulating one or more of said cells and bound virions in one or more emulsion droplets.

14. The method of claim 13, further comprising breaking said emulsion subsequent to said selective infection of one or more of said emulsified cells.

15. The method of claim 6, wherein said virion transfers one or more genetic elements into said cell upon infection of said cell.

16. The method of claim 1, further comprising: e) nucleic acid sequencing the recombinant product.

17. The method of claim 16, wherein said nucleic acid sequencing comprises deep sequencing or NextGeneration sequencing.

* * * * *